US007759546B2

(12) United States Patent
Scott

(10) Patent No.: US 7,759,546 B2
(45) Date of Patent: Jul. 20, 2010

(54) METHODS FOR MODIFYING PLANT ENDOSPERM

(75) Inventor: Roderick John Scott, Bath (GB)

(73) Assignee: University of Bath, Bath (GB)

( * ) Notice: Subject to any disclaimer, the term of this patent is extended or adjusted under 35 U.S.C. 154(b) by 358 days.

(21) Appl. No.: 10/058,825

(22) Filed: Jan. 30, 2002

(65) Prior Publication Data

US 2003/0074687 A1    Apr. 17, 2003

Related U.S. Application Data

(63) Continuation of application No. PCT/GB00/02953, filed on Jul. 31, 2000.

(30) Foreign Application Priority Data

Jul. 30, 1999 (GB) .................................. 9918061.4
Jul. 31, 2000 (WO) ..................... PCT/GB00/02953

(51) Int. Cl.
*C12N 15/82* (2006.01)
(52) U.S. Cl. ....................................... 800/285; 800/286
(58) Field of Classification Search ................. 800/278, 800/285, 290, 286; 536/23.1, 23.6; 435/468
See application file for complete search history.

(56) References Cited

U.S. PATENT DOCUMENTS

| 5,004,864 | A  | 4/1991  | Robertson et al. |   |
|-----------|----|---------|------------------|---|
| 5,204,253 | A  | 4/1993  | Sanford et al.   |   |
| 5,706,603 | A  | 1/1998  | Bergquiest et al.|   |
| 6,011,200 | A  | 1/2000  | Dellaporta et al.| 800/285 |
| 6,013,863 | A  | 1/2000  | Lundquist et al. |   |
| 6,255,561 | B1 | 7/2001  | Kossman et al.   |   |
| 6,320,106 | B1 | 11/2001 | Ertl et al.      |   |
| 6,329,567 | B1 | 12/2001 | Jofuku et al.    |   |
| 6,355,862 | B1 | 3/2002  | Handa et al.     |   |
| 6,429,356 | B1 | 8/2002  | Shewmaker        |   |
| 6,444,469 | B1 | 9/2002  | Dellaporta et al.| 435/468 |
| 6,455,688 | B1 | 9/2002  | Slabas et al.    |   |
| 6,459,019 | B1 | 10/2002 | Falco et al.     |   |
| 6,573,099 | B2 | 6/2003  | Graham           |   |
| 6,753,139 | B1 | 6/2004  | Baulcombe et al. |   |
| 6,897,359 | B2 | 5/2005  | Thompson et al.  |   |
| 6,900,368 | B2 | 5/2005  | Thompson et al.  |   |
| 6,906,244 | B2 | 6/2005  | Fischer et al.   |   |
| 6,940,001 | B1 | 9/2005  | Landschuetze     |   |
| 2003/0126642 | A1 | 7/2003 | Fischer et al.  |   |
| 2003/0135890 | A1 | 7/2003 | Fischer et al.  |   |
| 2003/0175783 | A1 | 9/2003 | Waterhouse et al.|   |
| 2004/0053876 | A1 | 3/2004 | Turner et al.    |   |

FOREIGN PATENT DOCUMENTS

| EP | 0 270 822 | 6/1988  |
|----|-----------|---------|
| EP | 0 117 618 | 7/1988  |
| EP | 0 242 246 | 11/1992 |
| EP | 0 344 029 | 1/1997  |
| WO | WO 98/04725 | 2/1998 |
| WO | WO 98/07834 | 2/1998 |
| WO | 99/53050    | 10/1999 |
| WO | WO 01/09299 | 2/2001  |

OTHER PUBLICATIONS

Fourgoux-Nicol et al (1999, Plant Molecular Biology 40 :857-872).*
Gutterson (1995, HortScience 30(5):964-966).*
Emery et al (2003, Current Biology 13:1768-1774).*
Mazzolini et al (1992, Plant Molecular Biology 20:715-731).*
Ronemus et al (1996, Science 273 (Aug. 2):654-657).*
Jacobsen et al (2000, Current Biology 10:179-186).*
Finnegan et al (1993, Nucleic Acids Res. 21:2383-2388).*
Finnegan et al (1996, PNAS 93:8449-8454).*
GenBank Accession No. C10692, Dec. 1998.
GenBank Accession No. U53501, May 1996.
GenBank Accession No. Z97335, Jun. 1999.
GenBank Accession No. AC002130, Aug. 2000.
GenBank Accession No. AC002396, Oct. 2002.
GenBank Accession No. AC002986, May 1998.
GenBank Accession No. AC007067, Jun. 2000.
GenBank Accession No. AF014824, Aug. 1997.
GenBank Accession No. AL021635, Feb. 1978.
GenBank Accession No. AL021711, Mar. 2000.
GenBank Accession No. AL035538, Feb. 1999.
Adams et al., "Parent-of-origin effects on seed development in *Arabidopsis thaliana* require DNA methylation," *Development*, 2000, 127(11):2493-2502.
Alexander and Wulff, "Experimental Ecological Genetics in Plantago: X. The Effects of Maternal Temperature on Seed and Seedling Characters in *P. lanceolata*," *J. Ecology*, 1985, 73(1):271-282.
Angenent et al., "A Novel Class of MADS Box Genes is Involved in Ovule Development in Petunia," *Plant Cell*, 1995, 7:1569-1582.
Bender and Fink, "Epigenetic Control of an Endogenous Gene Family Is Revealed by a Novel Blue Fluoroscent Mutant of *Arabidopsis*," *Cell*, 1995, 83:725-734.
Bevan, "Binary *Agrobacterium* vectors for plant transformation," *Nucleic Acids Res.*, 1984, 12(22):8711-8721.
Bhattacharya et al., "A mammalian protein with specific demethylase activity for mCpG DNA," *Nature*, 1999, 397:579-583.
Brink and Cooper, "The Endosperm in Seed Development," *The Botanical Review*, 1947, 13:423-541.
Brutnell and Dellaporta, "Somatic Inactivation and Reactivation of Ac Associated With Changes in Cytosine Methylation and Transposase Expression," *Genetics*, 1994, 138:213-225.
Chaudhuri and Messing, "Allele-specific parental imprinting of *dzr1*, a posttranscriptional regulator of zein accumulation," *Proc. Natl. Acad. Sci.* USA, 1994, 91:4867-4871.

(Continued)

Primary Examiner—Stuart F. Baum
(74) Attorney, Agent, or Firm—Fish & Richardson P.C.

(57) ABSTRACT

A method for controlling endosperm size and development in plants. The method employs nucleic acid constructs encoding proteins involved in genomic imprinting, in the production of transgenic plants. The nucleic acid constructs can be used in the production of transgenic plants to affect interspecific hybridisation.

27 Claims, 11 Drawing Sheets

OTHER PUBLICATIONS

Chaudhury et al., "Fertilization-independent seed development in *Arabidopsis thaliana*," *Proc. Natl. Acad. Sci.* USA, 1997, 94:4223-4228.

Chen et al., "Gene dosage and stochastic effects determine the severity and direction of uniparental ribosomal RNA gene silencing (nucleolar dominance) in *Arabidopsis* allopolyploids," *Proc. Natl. Acad. Sci.* USA, 1998, 95:14891-14896.

Colombo et al., "The Petunia MADS Box Gene *FBII* Determines Ovule Identity," *Plant Cell*, 1995, 7:1859-1868.

Duvick, "Genetic Contributions to Advances in Yield of U.S. Maize," *Maydica*, 1992, 37:69-79.

Ehlenfeldt and Ortiz, "Evidence on the nature and origins of endosperm dosage requirements in *Solanum* and other angiosperm genera," *Sex Plant Reprod.*, 1995, 8:189-196.

Finnegan et al., "Reduced DNA methylation in *Arabidopsis thaliana* results in abnormal plant development," *Proc. Natl. Acad. Sci.* USA, 1996, 93:8449-8454.

Foster et al., "A *Brassica napus* mRNA encoding a protein homologous to phospholipid transfer proteins, is expressed specifically in the tapetum and developing microspores," *Plant Science*, 1992, 84:187-192.

Fromm et al., "Stable transformation of maize after gene transfer by electroporation," *Nature*, 1986, 319:791-793.

Giroux et al., "A single gene mutation that increases maize seed weight," *Proc. Natl. Acad. Sci.* USA, 1996, 93:5824-5829.

Goto and Meyerowitz, "Function and regulation of the *Arabidopsis* floral homeotic gene *PISTILLATA*," *Genes & Development*, 1994, 8:1548-1560.

Grossniklaus et al., "Maternal Control of Embryogenesis by MEDEA, a Polycomb Group Gene in *Arabidopsis*," *Science*, 1998, 280:446-450.

Gruenbaum et al., "Sequence specificity of methylation in higher plant DNA," *Nature*, 1981, 292:860-862.

Guberac et al., "Influence of seed size on germinability, germ length, rootlet length and grain yield in spring oat," *Die Bodenkultur*, 1998, 49(1):13-18.

Haig and Westoby, "Genomic imprinting in endosperm: its effect on seed development in crosses between species, and between different ploidies of the same species, and its implications for the evolution of apomixis," *Phil. Trans. R. Soc. Lond. B*, 1991, 333:1-13.

Hannah and Greene, "Maize Seed Weight is Dependent on the Amount of Endosperm ADP-glucose Pyrophosphorylase," *J. Plant Physiol.*, 1998, 152:649-652.

Irish and Yamamoto, "Conservation of Floral Homeotic Gene Function between *Arabidopsis* and *Antirrhinum*," *Plant Cell*, 1995, 7:1635-1644.

Jack et al., "The Homeotic Gene *APETALA3* of *Arabidopsis thaliana* Encodes a MADS Box and Is Expressed in Petals and Stamens," *Cell*, 1992, 68:683-697.

Jones et al., "Methylated DNA and MeCP2 recruit histone deacetylase to repress transcription," *Nature Genetics*, 1998, 19:187-191.

Kakutani et al., "Characterization of an *Arabidopsis thaliana* DNA hypomethylation mutant," l*Nucleic Acids Res.*, 1995, 23:130-137.

Kakutani et al., "Developmental abnormalities and epimutations associated with DNA hypomethylation mutations," *Proc. Natl. Acad. Sci.* USA, 1996, 93:12406-12411.

Kass et al., "DNA methylation directs a time-dependent repression of transcription initiation," *Current Biology*, 1997, 7:157-165.

Kermicle and Alleman, "Gametic imprinting in maize in relation to the angiosperm life cycle," *Development*, 1990, Supplement, pp. 9-14.

Kiyosue et al., "Control of fertilization-independent endosperm development by the *MEDEA* polycomb gene in *Arabidopsis*," *Proc. Natl. Acad. Sci.* USA, 1999, 96:4186-4191.

Koltunow et al., "Apomixis: Molecular Strategies for the Generation of Genetically Identical Seeds without Fertilization," *Plant Physiol.*, 1995, 108:1345-1352.

Krannitz et al., "The Effect of Genetically Based Differences in Seed Size on Seedling Survival in *Arabibopsis thaliana* (Brassicaceae)," *Am. J. Botany*, 1991, 78(3):446-450.

Laherty et al., "Historic Deacetylases Associated with the mSin3 Corepressor Mediate Mad Transcriptional Repression," *Cell*, 1997, 89:349-356.

Li et al., "Role for DNA methylation in genomic imprinting," *Nature*, 1993, 366:362-365.

Lund et al., "Endosperm-specific demethylation and activation of specific alleles of α-tubulin genes of *Zea mays* L.," *Mol. Gen. Genet.*, 1995, 246:716-722.

Luo et al., "Genes controlling fertilization-independent seed development in *Arabidopsis thaliana*," *Proc. Natl. Acad. Sci.* USA, 1999, 96:296-301.

Manga and Yadav, "Effect of seed size on developmental traits and ability to tolerate drought in pearl millet," *J. Arid Environments*, 1995, 29:169-172.

Marshall, "Effect of Seed Size on Seedling Success in Three Species of *Sesbania* (Fabaceae)," *Amer. J. Bot.*, 1986, 73(4):457-464.

Martiensson and Richards, "DNA methylation in eukaryotes," *Curr. Opin. Genet. Dev.*, 1995, 5:234-242.

Matzke and Matzke, "How and Why Do Plants Inactivate Homologous (Trans)genes?" *Plant Physiol.*, 1995, 107:679-685.

Nan et al., "Transcriptional repression by the methyl-CpG-binding protein MeCP2 involves a histone deacetylase complex," *Nature*, 1998, 393:386-389.

Napoli et al., "Introduction of a Chimeric Chalcone Synthase Gene into Petunia Results in Reversible Co-Suppression of Homologous Genes *in trans*," *Plant Cell*, 1990, 2:279-289.

Ohad et al., "A mutation that allows endosperm development without fertilization," *Proc. Natl. Acad. Sci.* USA, 1996, 93:5319-5324.

Ohad et al., "Mutations in FIE, a WD Polycomb Group Gene, Allow Endosperm Development without Fertilization," *Plant Cell*, 1999, 11:407-415.

Pazin and Kadonaga, "What's Up and Down with Histone Deacetylation and Transcription?" *Cell*, 1997, 89:325-328.

Razin, "CpG methylation, chromatin structure and gene silencing—a three-way connection," *EMBO J.*, 1998, 17(17):4905-4908.

Reiser et al., "The *BELL1* Gene Encodes a Homeodomain Protein Involved in Pattern Formation in the *Arabidopsis* Ovule Primordium," *Cell*, 1995, 83:735-742.

Richards, "DNA methylation and plant development," *Trends in Genetics*, 1997, 13(8):319-323.

Roberts et al., "Gametophytic and sporophytic expression of an anther-specific *Arabidopsis thaliana* gene," *Plant J.*, 1993, 3(1):111-120.

Roeckel et al., "Phenotypic alterations and component analysis of seed yield in transgenic *Brassica napus* plants expressing the *tzs* gene," *Physiologia Plantarum*, 1998, 102:243-249.

Ronemus et al., "Demethylation-Induced Developmental Pleiotropy in *Arabidopsis*," *Science*, 1996, 273:654-657.

Schaal, "Reproductive Capacity and Seed Size in *Lupinus texensis*," *Amer. J. Bot.*, 1980, 67(5):703-709.

Scott et al., "Parent-of-origin effects on seed development in *Arabidopsis thaliana*," *Development*, 1998, 125:3329-3341.

Sessions et al., "Patterning the floral meristem," *Seminars in Cell & Developmental Biology*, 1998, 9:221-226.

Solter, "Differential Imprinting and Expression of Maternal and Paternal Genomes," *Annu. Rev. Genet.*, 1988, 22:127-146.

Stoskopf et al., "Chapter 17—Interspecific and Intergeneric Hybridization," *Plant Breeding—Theory and Practice*, 1993, Westview Press, Boulder, CO, pp. 345-371.

Vongs et al., "*Arabidopsis thaliana* DNA Methylation Mutants," *Science*, 1993, 260:1926-1928.

Winn, "Effects of Seed Size and Microsite on Seedling Emergence of *Prunella vulgaris* in Four Habitats," *J. Ecology*, 1985, 73:831-840.

Wulff, "Seed Size Variation in *Desmodium paniculatum*," *J. Ecology*, 1986, 74:99-114.

GenBank Accession No. L10692, dated Jul. 26, 1993.

GenBank Accession No. AJ002140, dated Apr. 15, 2005.

GenBank Accession No. AF007807, dated Feb. 19, 1998.

GenBank Accession No. AF034419, dated Mar. 2, 1998.

Bernacchia et al. "Carrot DNA-methyltransferase is encoded by two classes of genes with differing patterns of expression" *The Plant Journal*, 1998, 13(3):317-329.

Bestor and Verdine, "DNA methyltransferases" *Current Opinion in Cell Biology*, 1994, 6:380-389.

Bolitho et al., "Antisense apple ACC-oxidase RNA reduces ethylene production in transgenic tomato fruit" *Plant Science*, 1997, 122:91-99.

Bourque "Antisense strategies for genetic manipulations in plants" *Plant Science*, 1995, 105:125-149.

Carron et al., "Genetic modification of condensed tannin biosynthesis in *Lotus corniculatus*.1. Heterologous antisense dihydroflavonol reductase down-regulates tannin accumulation in "hairy root" cultures", 1994, TAG 87:1006-1015.

Colliver et al., "Differential modification of flavonoid biosynthesis with an antisense chalcone synthase construct in transgenic *Lotus corniculatus*" *Plant Molecular Biology*, 1997, 35:509-522.

Einset "Differential expression of antisense in regenerated tobacco plants transformed with an antisense version of a tomato ACC oxidase gene" *Plant Cell*, 1996, 46:137-141.

Elkind et al. "Abnormal plant development and down-regulation of phenylpropanoid biosynthesis in transgenic tobacco containing a heterologous phenylalanine ammonia-lyase gene" *PNAS*, 1990, 87:9057-9061.

Elomaa et al. "Transformation of antisense constructs of the chalcone synthase gene superfamily into *Gerbera hybrida*: differential effect on the expression of family members" *Molecular Breeding*, 1996, 2:41-50.

Faske et al. "Transgenic tobacco plants expressing pea chloroplast *Nmdh* cDNA in sense and antisense orientation" *Plant Physiol.*, 1997, 115:705-715.

Finnegan et al. "DNA Methylation in plants" *Annu. Rev. Plant Physiol. Plant Mol. Biol.*, 1998, 49:223-247.

Goll and Bestor "Eukaryotic cytosine methyltransferases" *Annu. Rev. Biochem.*, 2005, 74:481-514.

Herbik et al. "Isolation, characterization and cDNA cloning of nicotianamine synthase from barley" *Eur. J. Biochem.*, 1999, 265:231-239.

Hibino et al. "Increase of cinnamaldehyde groups in lignin of transgenic tobacco plants carrying an antisense gene for cinnamyl alcohol dehydrogenase" *Biosci. Biotech. Biochm.*, 1995, 59(5):929-931.

Jacobsen and Meyerowitz "Hypermethylated *SUPERMAN* epigenetic alleles in *Arabidopsis*" *Science*, 277:1100-1103, 1997.

Li et al., "An ARGONAUTE4-containing nuclear processing center colocalized with cajal bodies in *Arabidopsis thaliana*" *Cell*, 2006, 126:93-106.

Myers and Dean "Sensible use of antisense: how to use oligonucleotides as research tools" *TiPS*, Jan. 2000, 21:19-23.

Oliver et al. "Inhibition of tobacco NADH-hydroxypyruvate reductase by expression of a heterologous antisense RNA derived from a cucumber cDNA: Implications for the mechanism of action of antisense RNAs" *Mol. Gen. Genet.*, 1993, 239:425-434.

Ponger and Li "Evolutionary diversification of DNA methyltransferases in eukaryotic genomes" *Molecular Biology and Evolution*, 2005, 22:1119-1128.

Pontes et al. "*The Arabidopsis* chromatin-modifying nuclear siRNA pathway involves a nucleolar RNA processing center" *Cell*, 2006 126:79-92.

Salehuzzaman et al. "Isolation and characterization of a cDNA encoding granule-bound starch synthase in cassava (*Manihot esculenta* Crantz) and its antisense expression in potato" *Plant Molecular Biology*, 1993, 23:947-962.

Temple et al. "Modulation of glutamine synthetase gene expression in tobacco by the introduction of an alfalfa glutamine synthetase gene in sense and antisense orientation: molecular and biochemical analysis" *Mol. Gen. Genet.*, 1993, 236:315-325.

Trevanion et al. "NADP-Malate dehydrogenase in the $C_4$ plant *Flaveria bidentis*" *Plant Physiol.*, 1997, 113:1153-1165.

Van der Krol et al. "An anti-sense chalcone synthase gene in transgenic plants inhibits flower pigmentation" *Nature*, 1988, 333:866-869.

Veena et al. "Glyoxalase I from *Brassica juncea*: molecular cloning, regulation and its over-expression confer tolerance in transgenic tobacco under stress" *The Plant Journal*, 1999, 17(4):385-395.

Visser et al. "Inhibition of the expression of the gene for granule-bound starch synthase in potato by antisense constructs" *Mol. Gen. Genet.*, 1991, 225:289-296.

Bushell et al., "The Basis of Natural and Artificial Postzygotic Hybridization Barriers in *Arabidopsis* Species," *The Plant Cell*, 15:1430-1442 (2003).

Finnegan, E.J. and E.S. Dennis, "Isolation and identification by sequence homology of a putative cytosine methyltransferase from *Arabidopsis thaliana*," *Nucleic Acids Research* 21(10): 2383-2388 (1993).

Kinoshita et al., "Polycomb Repression of Flowering During Early Plant Development," *Proc. Natl. Acad. Sci.* USA, 98(24):14156-14161 (2001).

Liu et al., "Multiple Domains are Involved in the Targeting of the Mouse DNA Methyltransferase to the DNA Replication Foci," *Nucleic Acids Research*, 26(4):1038-1045 (1998).

Luo et al., "Expression and Parent-of-Origin Effects for FIS2, MEA, and FIE in the Endosperm and Embryo of Developing *Arabidopsis* Seeds," *Proc. Natl. Acad. Sci.* USA 97(19):10637-10642 (2000).

Merlo et al., "Ribozymes Targeted to Stearoyl-ACP Δ9 Desaturase mRNA Produce Heritable Increases of Stearic Acid in Transgenic Maize Leaves," The Plant Cell 10: 1603-1621 (1998).

Vikenoog et al., "Hypomethylation Promotes Autonomous Endosperm Development and Rescues Postfertilization Lethality in Fie Mutants," *The Plant Cell*, 12:2271-2282 (2000).

Yang et al., "Ribozyme-mediated high resistance against potato spindle tuber viroid in transgenic potatoes," *Proc. Natl. Acad. Sci.* USA 94: 4861-4865 (1997).

Genbank Accession No. AC093713, May 29, 2003.
Genbank Accession No. AF063403, May 14, 1998.
Genbank Accession No. AF096096, Jan. 25, 1999.
Genbank Accession No. AF129516, Apr. 6, 1999.
Genbank Accession No. AT5G49160, May 2, 2003.
Genbank Accession No. L05934, Oct. 23, 1999.
Genbank Accession No. U39944, Feb. 4, 2003.
Genbank Accession No. U76670, Jan. 23, 1997.
Genbank Accession No. U93215, Feb. 27, 2002.

Abler and Scandalios, "Isolation and characterization of a genomic sequence encoding the maize Cat3 catalase gene," *Plant Mol Biol.*, 1993, 22(6):1031-1038.

Altschul et al, "Gapped BLAST and PSI-BLAST: a new generation of protein database search programs" *Nucl. Acids Res.*, 1997, 25:3389.

Bateman et al, "Pfam 3.1: 1313 multiple alignments and profile HMMs match the majority of proteins," *Nucl. Acids Res.*, 1999, 27:260-262.

Bechtold et al., "*In planta Agrobacterium* mediated gene transfer by infiltration of adult *Arabidopsis thaliana* plants" *C.R. Acad. Sci.* Paris, 1993, 316:1194-1199.

Brummell et al., "Inverted repeat of a heterologous 3'-untranslated region for high-efficiency, high-throughput gene silencing," *Plant J.*, 2003, 33:793-800.

Bustos, et al., "Regulation of *B*-Glucuronidase Expression in Transgenic Tabacoo Plants by an A/T-Rich, *cis*,Acting Sequence Found Upstream of a French Bean *B*-Phaseolin Gene," *Plant Cell*, 1989, 1:839-854.

Cannon et al., "Organ-specific modulation of gene expression in transgenic plants using antisene RNA," *Plant Molecular Biology*, 1990, 15:39-47.

Ch'ng et al., "Antisense RNA complementary to 3' coding and noncoding sequences of creatine kinase is a potent inhibitor of translation in vivo," *Proc. Natl. Acad. Sci.* USA, Dec. 1989, 86:10006-10010.

Choi et al., "Control of Gene Imprinting in *Arabidopsis*," *XVIII International Congress on Sexual Plant Reproduction*, Beijing, China, Aug. 20-24, 2004.

Conceicao, "A cotyledon regulatory region is responsible for the different spatial expression patterns of *Arabidopsis* 2S albumin genes," *Plant*, 1994, 5:493-505.

Cao et al, "Locus-specific control of asymmetric and CpNpG methylatation by the DRM and CMT3 methyltransferase genes," *PNAS*, Dec. 10, 20002, 99(4):16491-16498.

Chuang et al., "Specific and heritable genetic interference by double-stranded RNA in *Arabidopsis thaliana*," *PNAS*, Apr. 25, 2000, 97(9):4985-4990.

Dorlhac de Borne et al., "Co-suppression of nitrate reductase host genes and transgenes in transgenic tobacco plants," *Mol. Gen. Genet.*, 1994, 243:613-621.

Flavell et al., "Developmental Regulation of Co-suppression in Petunia hybrida," *Current Topics in Microbiology and Immunology*, 1995, 197:43-56.

Gehring et al., "Imprinting and Seed Development," *The Plant Cell*, 2004, 16:S203-S213.

Green, et al., "Binding site requirements for pea nuclear protein factor GT-1 correlate with sequences required for light-dependent transcriptional activation of the *rbc*S-3A gene," *EMBO J.*, 1988, 7:4035-4044.

Hamilton et al., "A transgene with repeated DNA causes high frequency, post-transcriptional suppression of ACC-oxidase gene expression in tomato," *The Plant Journal*, 1998, 15(6):737-746.

Hamilton et al., "A Species of Small Antisense RNA in Post-transcriptional Gene Silencing in Plants," *Science*, Oct. 29, 1999, 286(5441):950-952.

Hoe-Huh, et al, "Regulation of Gene Imprinting in *Arabidopsis*," *Seed Development Symposium Sponsored by the Biology Department*, University of Saskatchewan, Canada, May 12-13, 2005.

Jeddeloh et al., "CCG methylation in angiosperms," *Plant J.*, 1996, 9:579-586.

Jordano, et al., "A Sunflower Helianthinin Gene Upstream Sequence Ensemble Contains an Enhancer and Sites of Nuclear Protein Interaction," *Plant Cell*, 1989, 1:855-866.

Jorgensen et al., "Altered gene expression in plants due to *trans* interactions between homologous genes," *TIB*, 8:340-344, 1990.

Jorgensen et al., "Do unintended antisense transcripts contribute to sense cosuppression in plants?," *TIG*, Jan. 1999, 15(1):11-12.

Kankel et al., "*Arabidopsis* Met1 Cytosine Methyltransferase Mutants," *Genetics*, Mar. 2003, 163:1109-1122.

Karlin et al, "Methods for assessing the statistical significance of molecular sequence features by using general scoring schemes," *Proc. Natl. Acad. Sci.*, 1990, 87:2264-2268.

Karlin et al, "Applications and statistics for multiple high-scoring segments in molecular sequences," *Proc. Natl. Acad. Sci.*, 1990, 90:5873.

Kishimoto et al., "Site specificity of the *Arabidopsis* MET1 DNA methyltransferase demonstrated through hypermethylation of the superman locus," *Plant Molecular Biology*, 2001, 46:171-183.

Lindroth et al., "Requirement of CHROMOMETHYLASE3 for Maintenance of CpXpG Methylation," *Science*, Jun. 15, 2001, 292:2077-2080.

Mascia et al., "Safe and acceptable strategies for producing foreign molecules in plants," *Current Opinion in Plant Biology*, 2004, 7:189-195.

Meier, et al., "Elicitor-Inducible and Constitutive in Vivo DNA Footprints Indicate Novel *cis*-Acting Elements in the Promoter of a Parsley Gene Encoding Pathogenesis-Related Protein 1," *Plant Cell*, 1991, 3:309-316.

Nakano et al., "A Tobacco NtMET1 cDNA Encoding a DNA Methyltransferase: Molecular Characterization and Abnormal Phenotypes of Transgenic Tobacco Plants," *Plant Cell Physiol.*, 2000, 41(4):448-457.

Niebel et al., "Co-suppression of B-1, 3-Glucanase Genes in *Nicotiana tabacum*," *Current Topics in Microbiology and Immunology*, 1995, 197:91-103.

Palauqui et al., "Field trial analysis of nitrate reductase co-suppression: a comparative study of 38 combinations of transgene loci," *Plant Molecular Biology*, 1995, 29:149-159.

PCR Primer: A Laboratory Manual, Dieffenbach, C. & Dveksler, G., Eds., *Cold Spring Harbor Laboratory Press*, 1995.

Ray, "*Arabidopsis* floral homeotic gene BELL (BEL1) controls ovule development through negative regulation of AGAMOUS gene (AG)," *Proc. Natl. Acad. Sci.* USA, 1994, 91:5761.

Robinson, "Altered gene expression in plants due to trans interactions between homologous genes," *TIBTECH*, Dec. 1990, 8:340-344.

Savidge et al., "Temporal Relationship between the Transcription of Two *Arabidopsis* MADS Box Genes and the Floral Organ Identity Genes," *The Plant Cell*, Jun. 1995, 7:721-733.

Sambrook et al., Molecular Cloning, A Laboratory Manual, 1989, Sections 9.37-9.52, $2^{nd}$ Edition, *Cold Spring Harbor Press*, Plainview; NY.

Saze et al, "Maintenance of CpG Methylation is essential for epigenetic inheritance during plant gametogenesis," *Nature Genetics*, May 2003, 34:65-69.

Sharp, "RNAi and double-strand DNA," *Genes & Development*, 1999, 13:139-141.

Sheehy et al., "Reduction of polygalacturonase activity in tomato fruit by antisense RNA," *Proc. Natl. Acad. Sci.* USA, Dec. 1988, 85:8805-8809.

Sheridan, "The *mac1* Gene: Controlling the Commitment to the Meiotic Pathway in Maize," *Genetics*, 1996, 142:1009-1020.

Smyth, "Gene silencing: Cosuppression at a distance," *Current Biology*, 1997, 7:R793-R795.

Sonnhammer et al, "Pfam: multiple sequence alignments and HMM-profiles of protein domains," *Nucl. Acids Res.*, 1998, 26: 320-322.

Sonnhammer et al, "Pfam: A comprehensive Database of Protein Domain Families Based on Seed Alignments," *Proteins*, 1997, 28:405-420.

Taylor, "Comprehending Cosuppression," *The Plant Cell*, Aug. 1997, 9:1245-1249.

Tuschl et al., "Targeted mRNA degradation by double-stranded RNA in vitro," *Genes & Development*, 1999, 13:3191-3197.

Urao, "Molecular cloning and characterization of a gene that encodes a MYC-related protein in *Arabidopsis*," *Plant Mol. Biol.*, 1996, 32:571-556.

Van der Krol et al, "Modulation of Eukaryotic Gene Expression by Complementary RNA or DNA Sequences," *BioTechniques*, 1988, 6(10):958-976.

Vaucheret et al., "Molecular and genetic analysis of nitrite reductase co-suppression in transgenic tobacco plants," *Mol. Gen. Genet.*, 1995, 248:311-317.

Voinnet et al., "Suppression of gene silencing: A general strategy used by diverse DNA and RNA viruses of plants," *PNAS*, Nov. 23, 1999, 96(24):14147-14152.

Wada et al., "Association between up-regulation of stress-responsive genes and hypomethylation of genomic DNA in tobacco plants," *Mol. Gen. Genomics*, 2004, 271:658-666.

Waterhouse et al., "Virus resistance and gene silencing in plants can be induced by simultaneous expression of sense and antisense RNA," *Proc. Natl. Acad. Sci.* USA, 1998, 95:13959-13964.

Xiao et al, "Imprinting of the MEA Polycomb Gene Is Controlled by Antagonism between MET1 Methyltransferase and DME Glycosylase," *Developmental Cell*, Dec. 2003, 5:891-901.

Yadegari et al., "Mutations in the FIE and MEA Genes that Encode Interacting Polycomb Proteins Cause Parent-of-Origin Effect on Seed Development by Distinct Mechanisms," *The Plant Cell*, 2000, 12:2367-2381.

Zhang, et al., "DNA Sequences That Activate Isocitrate Lyase Gene Expression during Late Embryogenesis and during Postgerminative Growth," *Plant Physio.*, 1996, 110:1069-1079.

\* cited by examiner

METHODS FOR MODIFYING PLANT ENDOSPERM

CROSS-REFERENCE TO RELATED APPLICATIONS

This application is a continuation of International Application No. PCT/GB00/02953, internationally filed Jul. 31, 2000, which was published in English, and claims priority to Great Britain Application No. 9918061.4, filed Jul. 30, 1999, the disclosures of both of which are incorporated in their entirety by reference hereto.

BACKGROUND OF THE INVENTION

1 Field of the Invention

The present invention relates to methods for controlling endosperm size and development, and seed viability in plants. The invention also relates to nucleic acid constructs for use in such methods, as well as modified plants per se.

2. Related Art

Yield in crop plants where seed is the harvested product is usually defined as weight of seed harvested per unit area (Duvick, 1992). Consequently, individual seed weight is regarded as a major determinant of yield. Most monocotyledonous plants e.g. maize, wheat, (see Esau, 1965) produce albuminous seeds—that is, at maturity they contain a small embryo and a relatively massive endosperm. Consequently, in monocotyledonous plants, the endosperm represents a significant component of seed yield. Endosperms accumulate and store diverse substances, including starch, proteins, oils and fats.

Therefore, in monocotyledons increasing the size of the endosperm or its ability to accumulate storage products is likely to increase individual seed weight and perhaps total yield.

Endosperms are utilised commercially in diverse ways, either indirectly as part of the whole seed or directly following their purification, or the purification of certain of their constituents. Hence endosperms may represent either a proportion or the entire commercial value of a crop. Examples of indirect usage include fodder maize and whole wheat flour. An example of direct usage of the complete endosperm is in the production of white flour for bread-making. Finally, maize oil represents an example of the utilisation of a constituent of the endosperm, but there are many others.

In contrast to monocotyledons, most dicotyledonous plants, e.g. oil seed rape, soybean, peanut, *Phaseolus vulgaris* (e.g. kidney beans, white beans, black beans), *Vicia faba* (broad bean), *Pisum sativum* (green pea), *Cicer aeietinum* (chick pea), and *Lens culinaris* (lentil) produce exalbuminous seeds—that is, mature seeds lack an endosperm. In such seeds the embryo is large and generally fills most of the volume of the seed, and accounts for almost the entire weight of the seed. In exalbuminous seeds the endosperm is ephemeral in nature and reaches maturity when the embryo is small and highly immature (usually heart/torpedo stage). Commonly embryo development depends on the presence of the endosperm, which is generally accepted to act as a source of nutrition for the embryo.

Scott et al (1998) showed that the size of the endosperm in terms of the number of endosperm cells at maturity in the dicotyledonous plant *Arabidopsis thaliana*, a close relative of oil seed rape (*Brassica napus*), is positively correlated with the weight of the mature seed. Plants that developed seeds with 80% smaller endosperms (average=80 nuclei) compared to controls (mean of 2x-2x (diploid plant crosses) and 4x-4x (tetraploid plant crosses)=400 nuclei) produced seeds that were 46% smaller (in weight terms=14 µg) than the controls (mean of 2x-2x and 4x-4x=30 µg). In contrast, plants that developed seeds with 160% bigger endosperms (average 640 nuclei) compared to controls (mean of 2x-2x and 4x-4=400 nuclei) produced seeds that were 180% larger (in weight terms=54 µg) than the controls (mean of 2x-2x and 4x-4x=30 µg). *Arabidopsis* seed in common with most other dicotyledonous seed is composed almost entirely of embryo. Hence the change in seed weight is almost completely due to a change in embryo weight.

Consequently, modifying endosperm size, in terms of the number of cells at maturity, has a dramatic impact on seed weight in seeds that do not contain endosperm at maturity. Without being bound by the following, one reasonable hypothesis is that a larger endosperm accumulates a greater quantity of reserves from the seed parent, perhaps by acting as a stronger "sink". These reserves then provide more resources for utilisation by the growing embryo, resulting in a larger seed. Alternative mechanisms might operate, however.

The seeds of dicotyledons, like those of monocotyledons are utilised in diverse ways. For example, pulses such as soybean, peanut, *Phaseolus vulgaris* (e.g. kidney beans, white beans, black beans), *Vicia faba* (broad bean), *Pisum sativum* (green pea), *Cicer aeietinum* (chick pea), *Lens culinaris* (lentil) are important world crops that are used directly for animal and human consumption. Seeds of oil rape, sunflower and linseed are processed to produce oils.

Clearly, despite the differences in the structure of monocot and dicot seeds, particularly with respect to the presence or absence of endosperm in mature seeds, the size of the endosperm is an important factor in determining individual seed weight, and therefore potentially total crop yield in plants where seed is the economic harvest. Indeed, Hannah and Greene (1998) showed that maize seed weight is dependent on the amount of endosperm ADP-glucose pyrophosphorylase, the enzyme responsible for supplying substrate for starch synthesis.

However, there is some evidence that an increase in seed weight is associated with a reduction in seed number in many breeding populations. Consequently, increasing individual seed size may not result in an increase in total yield. While maize breeding programmes have been successful and genetic improvement has played a significant role in increased maize yields, the genetic component to yield has led to only a doubling of this parameter since the 1930s (Duvick, 1992). The increase in maize yields is currently less than 1% per year.

The genetic basis for the resistance to increased seed weight encountered in conventional breeding programmes is not understood. However, Giroux et al (1996) showed that a single gene mutation in the endosperm specific gene shrunken2 of maize resulted in a seed weight increase of 11-18% without a reduction in seed number. This suggests that yield improvements are possible in a plant with a long history of intensive and successful breeding efforts, and may therefore be generally achievable. Similarly, Roekel et al. (1998) showed that introduction of the tzs gene into *Brassica napus* results in a significant increase in seed yield accounted for by increased seed number per silique and increased seed weight.

There is also evidence that seed size (weight) is positively correlated with a number of components of "seed quality" such as percent germination (Schaal, 1980: Alexander and Wulff, 1985; Guberac et al, 1998); time to emergence (Winn, 1985; Wulff, 1986); durability (survival under adverse growing conditions) (Krannitz et al, 1991; Manga and Yadav, 1995); growth rate (Marshall, 1986) and yield (Guberac et al, 1998). Seed quality is an important factor in the cost of production of commercial seed lots since these must be tested before sale. Consequently, increasing total seed weight, even without increases in total seed yield may have economic benefits through improvements in seed quality.

We have recently demonstrated (Scott et al., 1998) that hybridising *Arabidopsis* plants of different ploidies has reproducible and dramatic effects on the weight of progeny seed. For example, an interploidy cross between a diploid (2x) seed parent and a tetraploid (4x) pollen parent (2x-4x) results in seed which is 240% larger than 2x-2x seed. Conversely, 4x-2x crosses result in a reduced seed size (60% of 2x-2x). Analysis of endosperm development in these F1 seed reveals a clear correlation between final seed size and the size of the endosperm. In common with most dicots, endosperm is not present in the mature *Arabidopsis* seed but is required to nourish the developing embryo. Therefore, increased endosperm size translates into increased seed size by increasing embryo size, presumably by accumulating and then supplying increased nutrition, or by some other less direct means enabling the embryo to accumulate more resources from the mother.

In wild type 2x-2x crosses the endosperm is triploid and is formed by the fertilisation of a pair of fused haploid polar nuclei of maternal origin with a haploid sperm of paternal origin. Consequently, there is a 2:1 ratio of maternal to paternal genomes in the normal endosperms. An excess of paternal genomes in the endosperm, e.g. as a result of a 2x4x cross, causes increased endosperm proliferation (hyperplasia). An excess of maternal genomes in the endosperm (4x-2x crosses) has the opposite effect: decreased endosperm proliferation (hypoplasia).

Scott et al (1998) explain these observations in terms of the genomic imprinting (inactivation) of genes that contribute to endosperm vigour, either positively or negatively. Accordingly, paternal gametes have an overall positive effect on endosperm growth because genes that inhibit endosperm growth or functionality are imprinted, whilst genes that have a positive effect escape imprinting and are active in the endosperm. Adding more paternal genomes into the endosperm via a tetraploid pollen parent therefore increases the number of stimulatory genes resulting in a larger endosperm. Maternal genomes have the opposite effect. Importantly, imprinting effects have been recorded in a wide range of plant species including maize and *brassicas*. In mammals, a number of genes that influence foetal growth (typically expressed in the placenta) also exhibit uniparental expression due to imprinting during gametogenesis. Extra doses of these genes also have dramatic effects on embryo size.

Hybridisation is recognised as an important process for producing offspring having a combination of desirable traits from both parents. Hybridisation may be interspecific or intraspecific. Interspecific hybridisation is used for introducing desirable traits such as disease resistance into crop species. However, the ability to make successful sexual crosses is frequently restricted to closely related species because of the existence of a variety of pre-fertilisation and post-fertilisation reproductive barriers (see Stoskopf, Tomes and Christie, 1993). One type of post-fertilisation barrier is associated with poor or disrupted endosperm development (post-fertilisation endosperm development barrier), which results in non-viable seed (see Ehlenfeldt and Ortiz, 1995). Endosperm failure in unsuccessful crosses is due to the operation of a genetically determined system known as endosperm dosage (Haig and Westoby, 1991). Endosperm dosage is a form of genomic imprinting. The removal of the endosperm dosage barrier to sexual interspecific hybridisation would have economic benefits, since non-sexual techniques for hybridisation e.g. somatic hybridisation are costly and difficult.

The endosperm dosage system may also prevent intraspecific hybridisation where the parents are of different genomic constitutions (ploidies) (Haig and Westoby, 1991).

The occurrence of successful intra- and interspecific hybridisation can also be problematic. In particular, hybridisation between genetically modified crop plants and non modified cultivated or wild plants thereby creating hybrids carrying transgenes with the potential for environmental and other damage inherent in this form of "transgene escape", has caused alarm within both the public and the regulatory authorities.

There are various strategies that might be used to prevent transgene escape from crops into the wider environment. Critically, a range or spectrum of methods should be available to meet practical constraints imposed by the requirements of plant breeders and seed producers and the life histories of specific crop species when in the hands of farmers. For example, the complete elimination of flowering is acceptable in vegetable crops and forage grasses during the 'cropping stage', but unless this trait is conditional in some way, the production of seed by the seed producer, or the breeding of new varieties by the plant breeder, is rendered difficult or impossible.

In crops where the harvest is a fruit or a seed, given that most crop species are self-pollinating, the production of pollen, by at least the majority of flowers, is essential. Most of the major crops fall into this category.

Cleistogamous plants produce flowers that develop normally but which fail to open. Consequently, self pollination occurs, but no pollen escapes from the flower. Whilst this the implementation of this solution would 'only' require modifications to flower design, such an approach might be criticised on the grounds that pollen could escape from damage flowers.

The production of viable sexual hybrids occurs within species (intra-specific hybridisation) or between species (inter-specific hybridisation). However, in the case of inter-specific hybridisation, a successful outcome—viable hybrid seed—is usually only possible between closely related species. Two main barriers prevent hybridisation between more widely diverged species—inter-specific incompatibility at the stigma surface or within the style, which prevent fertilisation, and post-fertilisation barriers which cause seed abortion, usually through failures in endosperm development (Brink and Cooper, 1947; Ehlenfeldt and Ortiz, 1995).

Brink and Cooper (1947) working in *Lycopersicum* were the first to propose that the primary reason for the failure of inter-specific crosses was the same as for intraspecific crosses, namely failure of the endosperm itself. The operation of this type of barrier has been reported in numerous species including the *Brassicas* (see Haig and Westoby, 1991). These authors and others (see Ehlenfeldt and Ortiz, 1995) also proposed that endosperm failure in inter-specific crosses is due to an effective, rather than actual, imbalance in the normal ratio of maternal to paternal genomes in the endosperm. Different species are proposed to have different genomic strengths. Hence a cross between plants of the same ploidy may fail because the relative genomic strengths of their respective genomes result in a lethal effective genomic imbalance within the hybrid endosperm. Likewise a cross between two plants of different ploidies may succeed provided their relative genomic strengths result in a hybrid endosperm with a balanced genomic constitution. The setting of genomic strength is proposed to involve genomic imprinting, although the exact nature of the relationship is not understood.

In summary, the failure of intraspecific (interploidy) crosses and crosses between species may have a common cause—a genomic imbalance within the endosperm mediated by genomic imprinting. Modifying the genomic strength of one or both of a pair of species that normally hybridise may have application in generating a lethal relative endosperm imbalance, thereby creating a post fertilisation barrier between the two species. The same approach may have application in providing a post-fertilisation barrier within a species, for example between genetically-engineered crop varieties and non-engineered varieties. Practically, for transgene containment the genomic strength of the crop could be modified to prevent cross hybridisation with any problematic close relatives. Such a technology would facilitate the exploitation of genetically modified plants, with considerable economic and environmental benefits.

There is currently considerable research effort to develop transgenic technologies (see Koltunow et al., 1995) to introduce apomixis into crop species. In natural apomictic plant species 2n seed is produced without fertilisation of the egg. The genetic constitution of the embryo is therefore identical to that of the seed parent. The economic benefits of introducing an apomixis system into crop species include true breeding F1 hybrids. Currently, F1 hybrid seed is produced annually by hybridising two genetically distinct parents in a labour intensive and costly process. True breeding (apomictic) F1 hybrids could be propagated for sale without the hybridisation step. The removal of this step would potentially therefore reduce production costs.

An essential aspect of apomixis is that the embryo is derived from a cell with an unreduced (2n) number of chromosomes. In natural apomicts this is achieved by modifying meiosis (meiotic reconstitution) such that 2n gametes are produced, or deriving the embryo from a somatic cell with the 2n number of chromosomes. Irrespective of the origin of the embryo the endosperm is invariably derived via meiosis which is either restitutional or reductional. In the former case the two polar nuclei, which upon fertilisation produce the endosperm, are 2n and in the later case n. Given that natural apomicts utilise endosperms generated in this way it is likely to be the case for genetically engineered apomictic crop plants.

A potential problem in the development of apomictic crop species, given this likely dependency on 'sexual endosperms' (formed by fertilisation), is ensuring the successful development of the endosperm, since the endosperm is required to nourish the embryo or itself represents the principal economic harvest. One barrier to endosperm development is the endosperm dosage system. In species with an endosperm dosage system the ratio of maternal to paternal genomes in the endosperm is 2.1. Deviation from this ratio results in endosperm abortion and seed lethality (Haig and Westoby, 1991). Natural apomicts have adopted a number of strategies to ensure endosperm development. A few species (autonomous apomicts) develop a gynogenetic endosperm (maternal) in the absence of fertilisation of the polar nuclei. The majority however, retain fertilisation of the polar nuclei and maintain a 2:1 genomic ratio by modification of either male meiosis (to produce unreduced gametes) or the fertilisation process e.g. fertilisation involves only 1 polar nucleus. Still other species successfully deviate from the genomic 2:1 ratio.

For engineered apomixis the most attractive solution for ensuring endosperm development is the provision of autonomous endosperm development. Solutions involving fertilisation of the polar nuclei are likely to complicate the delivery of apomixis, for example by necessitating the introduction of a mechanism to prevent fertilisation of the "egg" or the need to devise ways to produce 2n male gametes, or by some other means ensure a 2:1 genomic ratio.

One approach to developing an autonomous apomict involves the induction and isolation of mutant genes that condition endosperm development in sexual species without fertilisation. Extensive screening efforts in *Arabidopsis* met with limited success having identified several mutant genes that condition only limited endosperm development in the absence of fertilisation (Ohad et al., 1996; Chaudhury et al., 1997; Ohad et al., 1999; Kiyosue et al., 1999; Luo et al., 1999). One potential explanation is that these mutations trigger endosperm development but do not overcome the effects of the endosperm dosage system. Endosperms in the mutants would have a genetic constitution of 2 maternal:0 paternal genomes, which deviates from the normal 2:1 genomic ratio. Significantly, Scott et al, 1998, recently showed that *Arabidopsis* possesses a dosage system capable of causing seed abortion where the ratio of parental genomes in the endosperm deviates significantly from 2:1.

Autonomous apomixis would enable the crop to produce seed without any requirement for pollen. Hence transgene escape through pollen could be prevented by arranging for the crop plant to carry any form of male sterility that stops the production or release of functional pollen.

The interploidy cross effect on seed size, the post-fertilisation endosperm development barrier to interspecific hybridisation and the barrier to autonomous endosperm development are all explicable in terms of genomic imprinting.

In mammals, a number of genes that influence foetal growth (typically expressed in the placenta) exhibit uniparental expression due to genomic imprinting during gametogenesis. Extra doses of these genes can have dramatic effects on embryo size (Solter, 1998). Genomic imprinting also prevents the development of gynogenetic or androgenetic (two paternal genomes, no maternal genome) embryos (Solter, 1998).

In mammals, genes selected for imprinting are maintained in an inactive state by DNA methylation. The enzyme responsible is DNA methyltransferase (MET) which is encoded by a single gene. Mice embryos containing an inactive DNA methyltransferase gene die at an early developmental stage and express both parental copies of genes that are normally imprinted (i.e. uniparentally expressed) (Li et al, 1993). This demonstrates the involvement of DNA methyltransferase in genomic imprinting and a requirement for imprinting in normal development.

In plants the imprinting mechanism is unknown. However, plant genomes contain relatively large amounts of the modified nucleotide 5-methylcytosine (Gruenbaum et al, 1981). Despite evidence implicating cytosine methylation in plant epigenetic phenomena, such as cosupression and inactivation of transposable elements (Napoli et al, 1990; Bender et al, 1995; Brutnell and Dellaporta, 1994, Martienssen et al ., 1995; Matzke and Matzke, 1995 ) the role of cytosine methylation in plant developmental processes and genomic imprinting remains unclear.

To date three different genes have been found that may be imprinted in the maize endosperm: tubulin (Lund et al 1995 ), a storage protein regulator gene dzr (Chaudhuri, and Messing, 1994) and the r gene transcription factor that regulates anthocyanin biosynthesis (Kermicle and, Alleman, 1990). In each case, the maternally inherited allele is undermethylated, over-expressed or both, whereas the paternally inherited allele is more methylated or has a reduced level of expression.

In *Arabidopsis*, ddm mutants (decrease in DNA methylation) have been isolated with reduced levels of cytosine methylation in repetitive sequences, although the mutations do not result in any detectable change in DNA methyltransferase activity (Vongs et al., 1993; Kakutani, 1995). After several generations of self pollination, ddm mutants exhibit a slight delay (1.7 days) in flowering, altered leaf shape, and an increase in cauline leaf number (Kakutani, et al, 1995). Repeated self pollination of ddm mutant plants does however result in the appearance of severe developmental abnormalities (Kakutani et al, 1996).

*Arabidopsis* plants expressing DNA methyltransferase 1(Met1) antisense (Met 1as) gene contain reduced levels of DNA methyltransferase activity and a correspondingly reduced level of general DNA methylation (Finnegan et al., 1996; Ronemus et al., 1996). In contrast to ddm mutants, *Arabidopsis* plants expressing a Met1as gene develop various developmental abnormalities at high frequency and without repeated self-fertilization, including floral abnormalities (Finnegan et al., 1996). PCT/US971/13358 also reports that *Arabidopsis* plants expressing a Met1as gene alter the rate of development of the plant. The development of the endosperm in ddm mutants and plants expressing Met1as has not been reported.

The present invention is based on the unexpected observation that a decrease of about 90% in the amount of methylated DNA present in a plant genome results in the production of gametes, both male and female, that behave in a manner that is consistent with the removal or attenuation of genomic imprinting. This is exemplified by the following experiments:

1. Endosperm development in seeds derived from a cross between a wild type 2x plant, as seed parent, and a 2x Met1as plant as pollen parent (2x-2xMet1as), resembles endosperm development in seeds derived from a 4x-2x interploidy cross (FIGS. 1 and 3).—the endosperm is small/underdeveloped. The resulting seed is smaller in weight terms than seed from control 2x-2x crosses (Table 1). Hence the male gametes from a Met1as plant behave like a female gamete from a wild type plant. This can be explained by proposing the removal or attenuation of imprinting in the male gamete.
2. Endosperm development in seeds derived from a cross between a 2xMet1as plant, as seed parent, and a wild type 2x plant as pollen parent, strongly resembles endosperm development in seeds derived from a 2x-4x interploidy cross between wild type plants (FIGS. 1 and 3).—that is, the endosperm is large/overdeveloped. The resulting seed is larger in weight terms than seed from control 2x-2x crosses (Table 1). Hence the female gametes from a 2xMet1as plant behave as a male genome of a normally methylated diploid plant. This can be explained by proposing the removal or attenuation of imprinting in the female gamete.
3. Reciprocal crosses between 2xMet1as and 4x wild type plants result in seed abortion (FIGS. 1 and 3); consequently seeds derived from these crosses are shrivelled and do not germinate (Table 1). The behaviour of the endosperm in seed generated in these crosses depends on the direction of the cross. Where the 4x plant is the seed parent the endosperm is extremely under-developed and contains very few endosperm nuclei and a very small chalazal endosperm (FIG. 1, Table 1). In contrast, where the 4x plant is the pollen parent the endosperm of the resulting seeds is over-developed, and contains many endosperm nuclei and a very well developed chalazal endosperm with many associated chalazal nodules (FIGS. 1 and 3, Table 1). This outcome resembles those obtained in crosses between 2x and 6x wild type plants which routinely fail to produce viable seed (FIG. 3) and display very under—(6x-2x) or over-developed (2x-6x) endosperm depending on the direction of the cross. These crosses represent examples of lethal parental genomic excesses within the endosperm that result from the large disparity between the ploidy level of the respective parents. The similarity between the outcomes and the behaviour of the endosperm in 2xMet1as—4x and 2x-6x reciprocal crosses can be explained by proposing that male and female gametes derived from 2xMet1as plants behave, in part, like gametes of the opposite sex with respect to genomic imprinting. This again strongly suggests that DNA hypomethylation caused by the Met1as gene removes or strongly attenuates genomic imprinting.
4. The behaviour of plants homozygous for the ddm mutation in reciprocal crosses with 2x and 4x wild type plants is very similar to that of plants homozygous for the Met1as gene (see FIG. 2 and Table 1). This strongly suggests that the basis of the interploidy cross effect is associated with general DNA hypomethylation.

BRIEF SUMMARY OF THE INVENTION

Thus, in a first aspect, the present invention provides a method for the production of modified endosperm which comprises the step of transforming a plant, or plant propagating material, with a nucleic acid molecule comprising one or more regulatory sequences capable of directing expression in the male or female germ line and/or gametes of the resultant plant and one or more sequences whose expression or transcription products(s) is/are capable of modulating genomic imprinting.

As will be described herein, modulation of imprinting of plant gamete DNA can be used alter endosperm development. The effects can be applied to male or female gametes of the transformed plant. Thus, in a second aspect, the present invention provides a method for the production of modified endosperm which comprises the step of transforming a plant, or plant propagating material, with a nucleic acid molecule comprising one or more regulatory sequences capable of directing expression within the developing gynoecium, especially the cell lineage that gives rise to the female germ line (megasporocyte tissue), within the ovule of the resultant plant and one or more sequences whose expression or transcription product(s) is/are capable of modulating genomic imprinting.

In a third aspect, the present invention provides a method for the production of modified endosperm which comprises the step of transforming a plant, or plant propagating material, with a nucleic acid molecule comprising one or more regulatory sequences capable of directing expression within the developing stamen, especially the cell lineage that gives rise to the male germ line (microsporocyte tissue) of the resultant plant and one or more sequences whose expression or transcription product(s) is/are capable of modulating genomic imprinting.

There are a number of proteins known or suspected to be involved in the process of genomic imprinting. Altering the rate of expression of those genes in the germ line of either sex can also be used to alter the development of the endosperm in a parent-specific manner.

In the African claw toad *Xenopus laevis*, the product of the methyl-cytosine binding protein 2 (MeCP2) has been shown to specifically bind to methylated cytosines (Kass et al., 1997; Jones et al., 1998). This protein, of which conserved homologs in mammals also exist, forms a complex at the C-met locus with several other proteins. Amongst these are the transcription-repression mSin3 proteins (Nan et al., 1998; Laherty et al., 1997) and a number of histone deacetylases (HDAC). The activity of the latter genes is presumed to be an important step in the process of anchoring histones to the DNA and hence the formation of heterochromatin and the silencing of genes (reviewed in Razin, 1998 and Pazin and Kadonaga, 1997). The MeCP2-protein may thus constitute the first step in the gene silencing process by guiding the heterochromatin-forming machinery to C-met loci. Interestingly, in contrast with this the protein has also been found to have a de-methylating function in that it removes methyl-groups from cytosine residues (Bhattacharya et al., 1999).

If the homologs of proteins in the C-met binding complex in plants are likewise involved in uniparental gene silencing (imprinting) then inactivation of these genes in the maternal or paternal germ lines would be predicted to mimic the uniparental inactivation of the genes responsible for methylation. In addition, there could be a cumulative effect if more than one gene is inactivated. If for instance inactivation of the MET1 gene by antisense transcription or ds-RNA in one of either germ lines is not complete, then introduction of an additional vector causing inactivation of one of the other components of the imprinting machinery will enhance the effect.

In a preferred aspect, the present invention provides a method for the production of modified endosperm based on targeting the germ line or gametes with transgenes which alter the capacity of genes to form, maintain or express imprints. This can be achieved in a number of ways. Firstly, by incorporation of one or more sequences encoding proteins associated with the application or maintenance of genetic imprints. Specifically, such sequences may encode a histone deacetylase, methyl cytosine binding protein or Sin 3 proteins, for example, m Sin 3.

Alternatively, the transgene may incorporate sequences including the FIE gene or the FIS gene, for example fis1, fis2 or fis3.

Imprinted genes may also contain, or be located close to, signals within the DNA sequence (a particular nucleotide sequence motif) that mark them out for imprinting during gamete production. Such a motif may, in addition to expressed proteins associated with the formation and/or maintenance of genomic imprints, be involved in the formation of an "imprinting complex". It is contemplated that removing or inactivating the DNA motif, or restricting the availability of the associated proteins, in the imprinting complex may provide a means for preventing or attenuating the application of imprints, thereby allowing the expression of genes which may otherwise be silenced in the endosperm.

DETAILED DESCRIPTION OF THE INVENTION

The present invention further provides methods for removing or attenuating genomic imprinting, based on targeting the germ line or gametes with transgenes which alter the methylation pattern of genes, or their capacity to form or maintain imprints, within the developing endosperm. Thus, in a fourth aspect, the present invention provides a method for the production of modified endosperm, which comprises the step of transforming a plant, or plant propagating material, with a nucleic acid molecule comprising one or more regulatory sequences capable of directing expression in the male or female germ line and/or gametes of the resultant plant, and one or more sequences whose expression or transcription product(s) is/are capable of altering the degree of methylation of nucleic acid.

The restriction of imprint removal or attenuation to one or other sex of gamete is desirable for 3 reasons:
1. To provide for removal of imprinting in a single sex of gamete within an individual plant. This will produce the asymmetry of imprinting that is required to mimic the interploidy cross effect in a self-fertilising plant.
2. To prevent developmental abnormalities that are associated with generalised hypomethylation, such as occurs with the CaMV35S driven Met1 antisense gene.
3. To prevent the attenuation of the interploidy cross effect due to the expression of the hypomethylation gene (Met1as) within the endosperm. Crosses between two 2xMet1as plants result in seed with a slightly increased number of endosperm nuclei and normal seed weight (Table 1), which is most easily explained by proposing that the combination of hypomethylated gametes of both sexes allows normal endosperm development The important property of the nucleic acid molecule used in the transformation step is that DNA of cells that contribute to one sex of germ line is subject to alteration of the pattern of DNA methylation through the activity of the transgenes. The germ-line is the tissue within the reproductive organs that produces the gametes. In the anthers (stamen) this is the microsporogenous cell tissue and in the pistil (gynoecium) the megasporocyte tissue.

Since the timing of the application of the genomic imprints is currently not known the activity of the regulatory sequences, e.g. promoters (or fragments of promoters) promoters should be as broad as possible whilst remaining consistent with the principles discussed herein.

As will be described herein, alteration of the methylation of plant gamete DNA can be used to modify endosperm development. Thus, in a fifth aspect, the present invention provides a method for the production of modified endosperm, which comprises the step of transforming a plant, or plant propagating material, with a nucleic acid molecule comprising one or more regulatory sequences capable of directing expression within the developing gynoecium, especially the cell lineage that gives rise to or comprises the female germ line (megasporocyte tissue), within the ovule of the resultant plant, and one or more sequences encoding one or more proteins which cause methylation or demethylation of nucleic acid.

In this aspect of the invention, the resultant endosperm is larger, and the seed produced is heavier. Herein, suitable promoters include promoter fragments from the *Arabidopsis* AGL5 gene (Sessions et al., 1998), the Petunia FBP7 and FBP11 genes (Angenent et al., 1995; Colombo et al.,1995), *Arabidopsis* BEL1 gene (Reiser et al., 1995), *Arabidopsis* MEDEA (FIS1) gene (Grossniklaus et al., 1998; Kiyosue et al., 1999), *Arabidopsis* FIS 2 (Kiyosue et al., 1999), FIE (FIS 3) (Ohad et al., 1999; Kiyosue et al., 1999), orthologs/homologues of these genes from other species. Other promoters that drive expression that is restricted to cells within the female reproductive organs that contribute to the female germ line would also be suitable. Especially suitable are promoters from gynoecium-specific genes that are first expressed during early gynoecium development, preferably before the differentiation of individual ovules, and which maintain their expression until ovule differentiation is complete (contain egg cell and binucleate central cell).

As used herein, the term "homologues"0 of the genes is defined to include nucleic acid sequences comprising the identical sequence to the gene or a sequence which is 40% or more identical, preferably though 45%, 50%, 55%, 60%, 65%, 70%, 75%, 80%, 85%, 90%, 95% to the sequence of the gene at the nucleic acid residue level, using the default parameters of the GAP computer program, version 6.0 described by Deveraux et al, 1984 and available from the University of Wisconsin Genetics Computer Group (UWGCG). The GAP program utilises the alignment method of Needleman and Wunsch 1970 as revised by Smith and Waterman 1981.

In a sixth aspect, the present invention provides a method for the production of modified endosperm which comprises the step of transforming a plant, or plant propagating material, with a nucleic acid molecule comprising one or more regulatory sequences capable of directing expression within the developing stamen, especially the cell lineage that gives rise to or comprises the male germ line (microsporocyte tissue) of the resultant plant and one or more sequences encoding one or more proteins which cause methylation or demethylation of nucleic acid.

In this aspect of the invention, the resultant endosperm is smaller, and hence the seed is lighter.

Herein, suitable promoters include promoter fragments derived from the *Arabidopsis* genes APETALA3 (Jack et al., 1992; Irish and Yamamoto, 1995), the *Arabidopsis* PISTILATTA gene (Goto and Meyerowitz, 1994), the *Arabidopsis* E2 (Foster et al., 1992), the *Arabidopsis* APG (Roberts et al., 1993), homologues/orthologs of these genes from other species. Other promoters that drive expression that is restricted to cells within the male reproductive organs that contribute to the male germ line would also be suitable. Especially suitable are promoters from stamen-specific genes that are first expressed during early stamen development, preferably before the differentiation of individual microsporocytes, and which maintain their expression until stamen differentiation is complete.

Herein, promoters that drive gene expression in cells of the germ line or in cells that represent the direct progenitors of the germ line within either the stamen or pistil and which, when in conjunction with the Met1as gene, produce hypomethylated gametes are referred to as 'germ line' promoters.

Thus, as will be appreciated by the skilled person, the present invention allows for the modification of the endosperm such that it is either increased or decreased in size. In addition, the development of the endosperm can be altered such that the modified plants can be used in carrying out intraspecific hybridisation, erecting artificial barriers to intra- and interspecific hybridisation to prevent "transgene escape", or in engineering apomixis.

In one specific embodiment, the degree of methylation is increased. This can readily be achieved by incorporating one or more sequences encoding one or more methylating enzymes into the transgene.

Examples of Suitable Methylating Enzymes Include:

i) Methylase 1 (acc. nr. L10692;
ii) Methylase 1-like gene (acc. nr. Z97335);
iii) Methylase 2 (acc. Nr AL021711); and
iv) Chromomethylase (acc. Nr. U53501);
all from *Arabidopsis*.

In another specific embodiment, the degree of methylation is decreased. This can be achieved in a number of ways. Firstly, by incorporation of one or more sequences encoding one or more demethylating enzymes, such as de-methylase (=MeCP2-homologue; see below) (acc. nr. AL021635) into the transgene. Alternatively, the transgene can incorporate sequences which cause down regulation of methylating enzymes already present in the plant. For instance, one can use antisense sequences, e.g. the Met1as "gene". In addition, it has been found that incorporation of whole or partial copies of an already present gene can result in suppression of gene expression. Thus, the transgene can incorporate additional copies, or partial copies, of genes encoding methylating enzymes already present in the plant. In another alternative, the transgene can incorporate a sequence encoding a ribozyme.

With respect to the sequence, or sequences capable of altering the degree of methylation, sequences encoding methylating or demethylating enzymes can be used. Examples of the latter include:

1) Methylase 1-like gene (acc. nr. Z97335);
ii) Methylase 2 (acc. nr. AL021711);
iii) Chromomethylase (acc. nr. U53501);
iv) de-methylase (=MeCP2-homologue; see below)(acc. nr. AL021635);

In *Arabidopsis*, possible homologs of the following genes have been found:

MeCP2 (acc nr. AL021635)
HDAC1/2 (acc. nr. AF014824 & AL035538)
mSIN3 (acc. nr. AC007067_5 & AC002396)
_p300: a histone acetylation-gene (acc. nr. AC002986.1 & AC002130.1)

In a seventh aspect, the present invention provides an isolated or recombinant nucleic acid molecule, eg a DNA molecule, which comprises one or more regulatory sequences capable of directing expression in the male or female germ line and/or gametes of a plant and one or more sequences capable of altering the degree of methylation of nucleic acid.

In a preferred embodiment of the seventh aspect, the degree of nucleic acid methylation is decreased. An eight aspect of the present invention provides the use of a transgene in which the degree of nucleic acid methylation is decreased, as a post-fertilisation barrier to hybridisation, for example, interspecific or intraspecific hybridisation between plants.

The expression "barrier" is defined to include all forms of reproductive barrier which are associated with poor or disrupted endosperm development. Specifically, the term barrier refers to a post-fertilisation endosperm development barrier, which results in non-viable seed.

The transgene provides a barrier to hybridisation by modifying the genomic strength of one or both a pair that normally hybridise thereby causing an effective genomic imbalance leading to failed or disrupted endosperm development. The genomic strength may be modified by removing or attenuating genomic imprinting through DNA hypomethylation. The advantage of preventing hybridisation between plants of the same species (interspecific hybridisation) is discussed earlier in the application in the context of preventing transgene escape.

In a ninth aspect, the present invention provides the use of a transgene in which the degree of nucleic acid methylation is decreased, in overcoming a post-fertilisation barrier to hybridisation. In this context, the barrier to hybridisation between plants of the same species (interspecific hybridisation) arises through endosperm dosage which leads to failed endosperm development. The removal or attenuation of genomic imprinting through DNA hypomethylation, may remove the endosperm dosage barrier to interspecific hybridisation. The removal of the endosperm dosage barrier to several interspecific hybridisation would have economic benefits as discussed previously in the application.

The nucleic acid of the seventh aspect of the invention will normally be employed in the form of a vector and such vectors form a further aspect of the invention.

The vector may be for example a plasmid, cosmid or phage. Vectors will frequently include one or more selectable markers to enable selection of cells transfected or transformed and to enable the selection of cells harbouring vectors incorporating heterologous DNA. Examples of such a marker gene include antibiotic resistance (EP-A-0242246) and glucuronidase (GUS) expression (EP-A-0344029). Expression of the marker gene is preferably controlled by a second promoter which allows expression in cells other than the gametes, thus allowing selection of cells or tissue containing the marker at any stage of regeneration of the plant. The preferred second promoter is derived from the gene which encodes the 35S subunit of Cauliflower Mosiac Virus (CaMV) coat protein. However any other suitable second promoter could be used.

Cloning vectors may be introduced into *E. coli* or another suitable host which facilitate their manipulation. DNA in accordance with the invention will be introduced into plant cells by any suitable means. Thus, according to yet a further aspect of the invention, there is provided a plant cell including DNA in accordance with the invention.

DNA may be transformed into plant cells using a disarmed Ti-plasmid vector and carried by agrobacterium by procedures known in the art, for example as described in EP-A0117618 and EP-A-0270822. Alternatively the foreign DNA could be introduced directly into plant cells using a particle gun. This method may be preferred for example when the recipient plant is a monocot.

A whole plant can be regenerated from a single transformed plant cell, thus in a further aspect the present invention provides transgenic plants (or parts of them such as propagating material) including DNA in accordance with the invention. The regeneration can proceed by known methods. When the transformed plant flowers it can be seen to be male sterile by the inability to produce viable pollen. Where pollen is produced it can be confirmed to be non-viable by the inability to effect seed set on a recipient plant.

The present invention also provides transgenic plants and the sexual and/or asexual progeny thereof which have been transformed with a recombinant DNA sequence according to the invention. The regeneration of the plant can proceed by any known convenient method from suitable propagating material.

A further aspect of the present invention provides a method for manipulating genomic imprinting in a plant, which comprises the step of transforming a plant, or plant propagating material, with a nucleic acid molecule comprising one or more regulatory sequences capable of directing expression in the male or female germ line and/or gametes of the resultant plant, and one or more sequences whose expression or transcription product(s) is/are capable of altering the degree of methylation of nucleic acid.

Preferred features for each aspect of the invention are as for each other aspect *mutatis mutandis*.

The present invention will now be described with reference to the following examples, which should not be construed as in any way limiting the invention. The examples are accompanied by the following figures:

BRIEF SUMMARY OF THE DRAWINGS

FIG. 10—Seeds from a fie-1/FIE X FIE/FIE cross. (A) Light micrograph showing the two classes of seeds, plump (pl) and shrivelled (sh). (Bar=5 micrometers). (B-G) Confocal micrographs of normal (B-D) and aborting (E-G) seeds at 8 DAP, centred on micropylar (B, E), central (C, F), and chalazal (D,G) regions of the embryo sac. The endosperm in (E-G) is overgrown and has not cellularized. Bar=50 micrometers.

EXAMPLES

Example 1

The Use of Gametes from Hypomethylated Plants (Met1as and ddm) Mimics the Interploidy Cross Effect (Alters Number of Endosperm Nuclei Formed and Consequently the Weight of Mature Seed)

Reciprocal interploidy (different.ploidy) crosses between diploid (2x), and tetraploid (4x) (Scott, et al 1998) or hexaploid (6x) (Scott, et al 1998) *Arabidopsis* plants result in changes to both the size of the endosperm, in terms of the number of endosperm nuclei and volume of the chalazal endosperm, and to the dry weight of mature seeds (see Table 1) and the viability of the seed (Table 1). This is the interploidy cross effect.

Crosses Involving Met1as Plants

Figure 1:
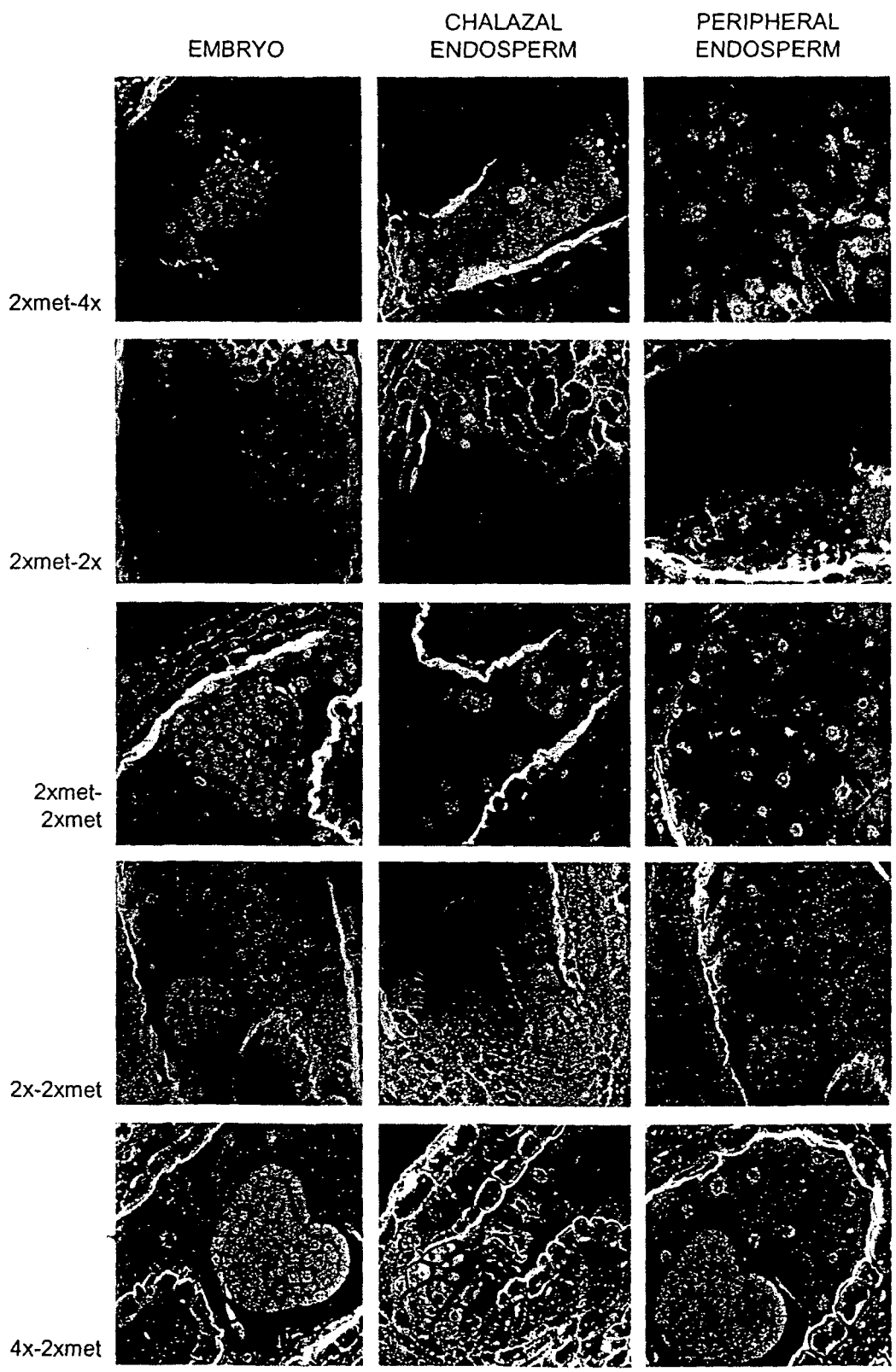
FIG. 1—Embryo and endosperm development following crosses with met1-antisense expressing plants as a parent. Confocal micrographs of Feulgen-stained seeds 4-6 days after pollination. Column 1, embryo; column 2, chalazal endosperm; column 3, peripheral endosperm. Note a paternal excess phenotype (over developed chalazal endosperm, highly proliferated peripheral endosperm) in crosses with a demethylated plant as the mother (row 1, 2) and a maternal excess phenotype (small or absent chalazal endosperm and a poorly developed peripheral endosperm) in crosses with a demethylated plant as the father (row 4,5). See text for full details.
Figure 2:
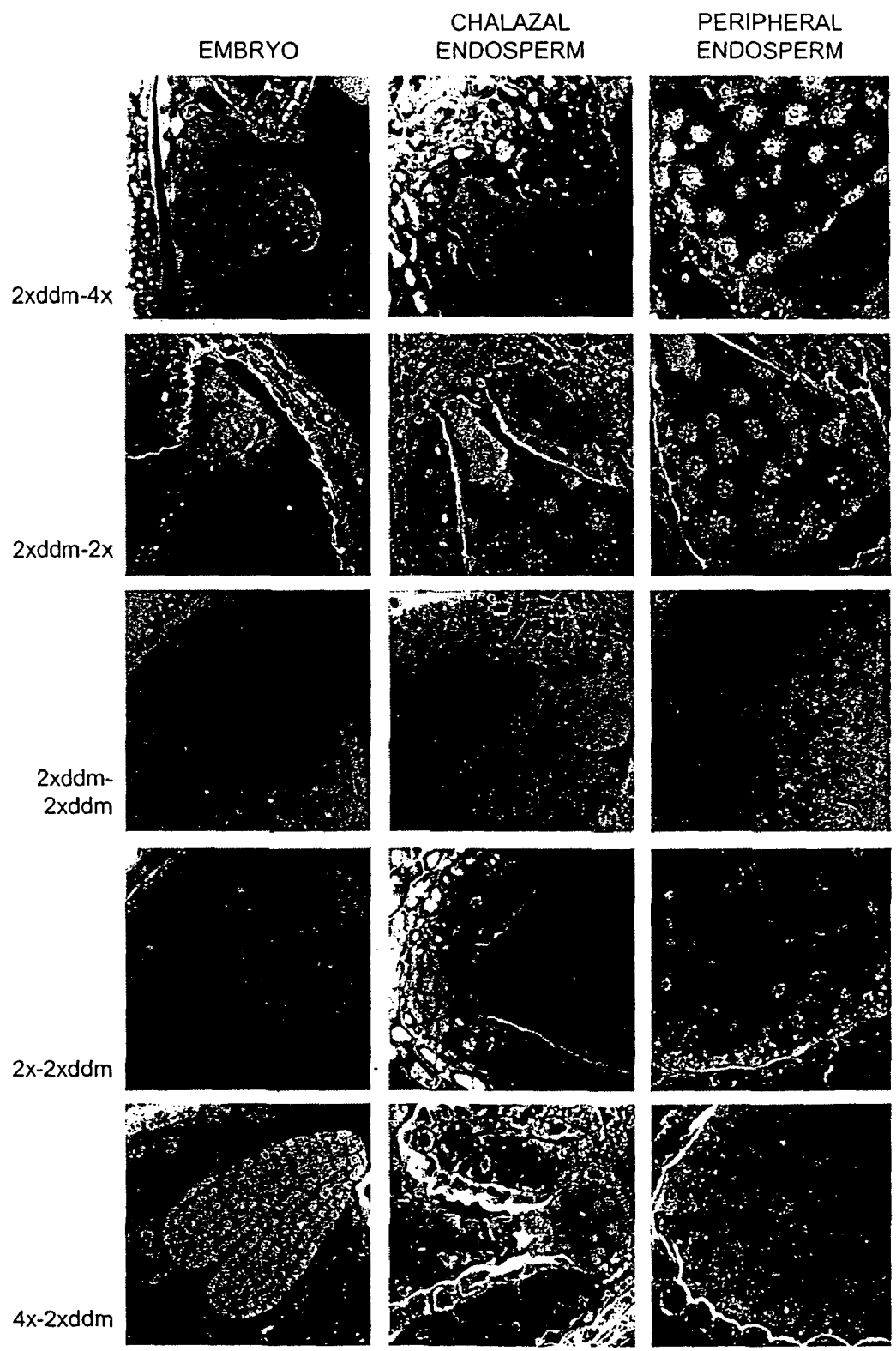
FIG. 2—Embryo and endosperm development following crosses with ddm1-mutant plants as a parent. Confocal micrographs of Feulgen-stained seeds 4-6 days after pollination. Column 1, embryo; column 2, chalazal endosperm; column 3, peripheral endosperm. See text for full details.
Figure 3:
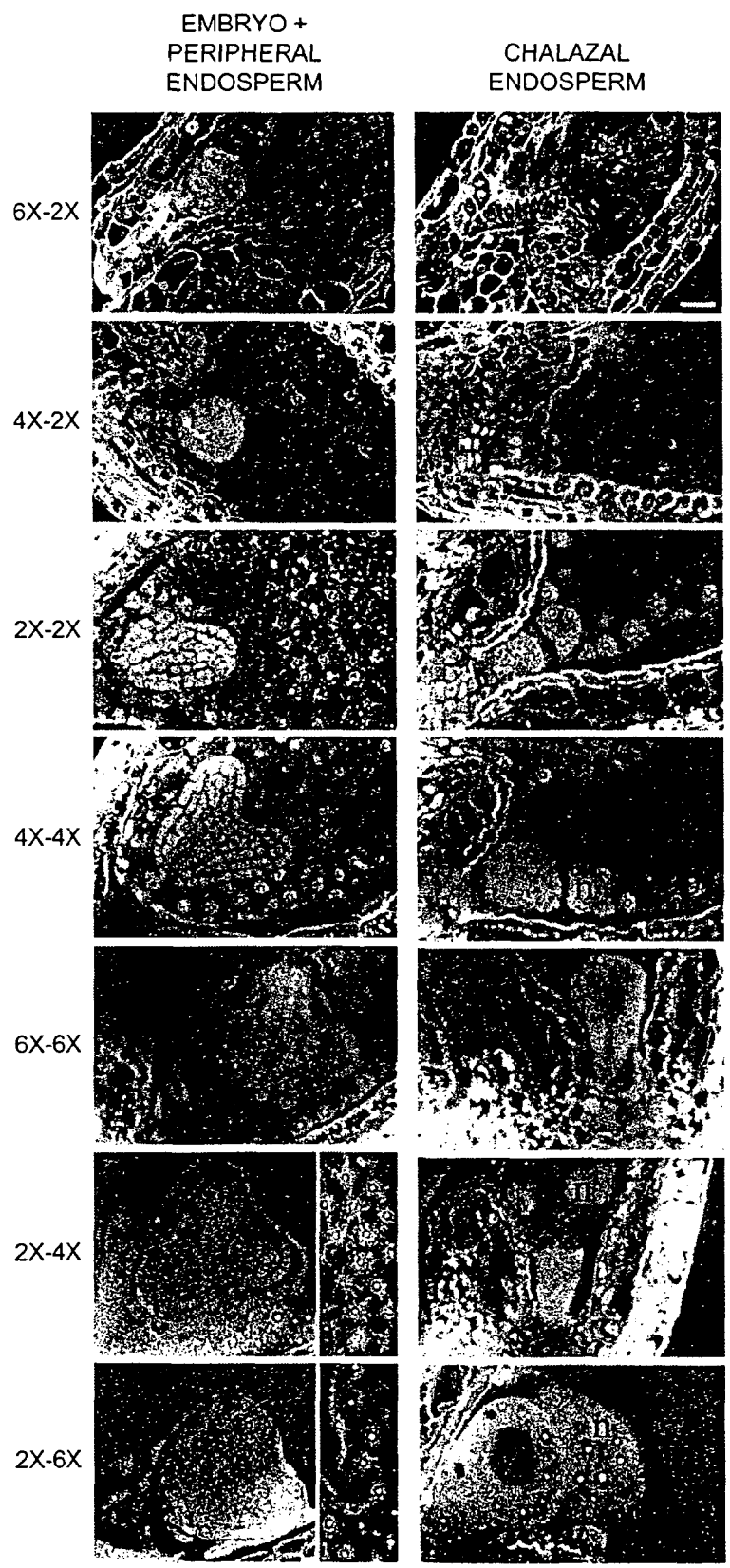
FIG. 3—Embryo and endosperm development following interploidy crosses and balanced crosses. Confocal micrographs of Feulgen-stained seeds 4-6 days after pollination. Column 1, embryo+peripheral endosperm; column 2, chalazal endosperm. For the 2x-4x and 2x-6x crosses (row 6, 7) the peripheral endosperm is shown as an inset. See text for full details.

Intraploidy (same ploidy) crosses between 2x Met1as plants and 2x wild type plants mimic this effect (see Table 1 and FIGS. 1 and 3). A cross between a 2x Met1as plant as seed parent and a 2x wild type plant as pollen parent produces seeds with an average of 450 endosperm nuclei (an increase of 130% over 2xmet-2xmet cross), a relative increase in chalazal endosperm volume of 75% compared to 2xmet-2xmet seed, and a mature dry weight of 20 µg (an increase of 33% compared to seed from 2xmet-2xmet cross) (see Table 1).

A cross between a 2x wild type plant as seed parent and a 2x Met1as plant as pollen parent produces seeds with an average of 200 endosperm nuclei (a reduction of 43% over 2xmet-2xmet cross), a relative decrease in chalazal endosperm volume of 50% compared to 2xmet-2xmet seed, and a mature dry weight of 10 µg (a decrease of 30% over a wild type 2xmet-2xmet cross) (see Table 1).

TABLE 1

Outcomes of control crosses and crosses involving Met1 antisense and ddm mutant plants

| Cross | Interploidy cross phenotype[1] | Viability of hybrid seed (%)[2] | Maximum number of peripheral endosperm nuclei[3] | Relative volume of chalazal endosperm[4] | Relative change to cellularisation time (days)[5] | Seed weight (µg)[6] |
|---|---|---|---|---|---|---|
| 2x-2x | NA | 95–100 | 400 | 1 | 0 | 22 |
| 4x-4x | NA | 95–100 | 400 | 2.5 | 0 | 36 |
| 6x-6x | NA | 95–100 | 300 | 3.5 | 0 | 44 |
| 2x-4x | PE | 95–100 | 640 | 2 | +1 | 54 |
| 4x-2x | ME | 95–100 | 80 | 0.6 | −1 | 14 |
| 2x-6x | PE | 0[7] | 400 | 6.8 | absent | 6 |
| 6x-2x | ME | 0[7] | 50 | 0.2 | −1.5 | 4 |
| 2xmet-2xmet | PE | 95–100 | 350 | 1 | 0 | 15 |
| 2xmet-2xmet |  | (90)[8] | (598)[8] |  |  | (13.6)[8] |
| 2x-2xmet | ME | 95–100 | 200 | 0.5 | −0.5 | 10 |
| 2x-2xmet |  | (93)[8] | (227)[8] |  |  | (9.5)[8] |
| 2xmet-2x | PE | 95–100 | 450 | 1.75 | +0.5 | 20 |
| 2xmet-2x |  | (97)[8] | (1,365)[8] |  |  | (32.5)[8] |
| 2xddm-2xddm | PE | 95–100 | 350 | 1.25 | 0 | 19 |
| 2x-2xddm | ME | 95–100 | 250 | 0.5 | −0.5 | 12 |
| 2xddm-2x | PE | 95–100 | 400 | 2 | +0.5 | 21 |
| 4x-2xmet | ME | 0[7] | 100 | 0.3 | −1.5 | 3 |
| 2xmet-4x | PE | 0[7] | 740 | 4.4 | >+3 | 15 |
| 4x-2xddm | ME | 0[7] | 150 | 0.3 | −1.5 | 5 |
| 2xddm-4x | PE | 0[7] | 680 | 3.5 | >+3 | 5 |

NA, not applicable; PE, paternal excess; ME, maternal excess.
[1]either paternal (PE) or maternal (ME) excess as defined in Scott et al., 1998.
[2]determined by germination on soil.
[3]counts done as described in Scott et al., 1998.
[4]calculated relative to amount in 2x-2x control cross at heart stage (approx. 5 DAP).
[5]expressed relative to 2x-2x control cross (usually 5 DAP).
[6]measured as described in Scott et al., 1998.
[7]seeds shriveled.
[8]this experiment was performed subsequent to the experiment that yielded the non-bracketed data and use improved growing technique for the met1a/s plants. This resulted in more vigorous plant which presumably accounts for the observed changes in seed weight. Note however that the changes are qualitatively the same as the original experiment ie. 2x-2xmet are small than 2xmet-2xmet and 2xmet-2x are larger.

The presence and (possible) activity of the Met1a/s gene within the endosperm potentially complicates the interpretation of the data produced in out crosses involving homozygous Met1a/s plants. In such crosses the endosperm (and embryo) inherit a single copy of the Met1as, either from the seed or pollen parent. If the Met1as is active within the endosperm it may, 1. disrupt endosperm development since Met1as plants show various vegetative and floral abnormalities associated with the mis-expression of certain genes that regulate development (Finnegan, 1996). However, the presence of the Met1as gene does not appear to have this effect since the endosperms of seeds derived from self pollinated Met1as plants appear developmentally normal except for a degree of paternal excess (FIG. 1).
2. attenuate the magnitude of the interploidy cross effect, by demethylating and thereby erasing imprints from the genome contributed by the normally methylated parent. The imprints must be maintained and propagated in the endosperm if the interploidy cross effect is to be mimicked. The removal of imprints via the action of the Met1as gene could reactivate imprinted loci such that the endosperm genomes behave as if derived from same ploidy parents.

To demonstrate that the interploidy cross effects described above are due to the effect of the Met1as gene on the imprinting of gametes rather than any effect within the endosperm we present data from crosses involving plants hemizygous (that is carrying a single copy) of the Met1as gene. Such plants show patterns of general DNA demethylation similar to homozygotes. Hence gametes derived from these plants are generated in a hypomethylating environment, but because the plants are hemizygous only 50% of these gametes contain the Met1as gene. This enables gametes to be produced in a demethylating environment which then do not subsequently contribute a Met1as into the endosperm when used in crosses. This allows the effect of removing imprints within the gametes to be evaluated in endosperms that do not contain the Met1as gene.

The results of reciprocal crosses involving hemizygotes and 4x wild type plants are shown in Table 2. Both crosses result in a 1:1 ratio of plump, viable: shrivelled, inviable seed. The shrivelled seeds are assumed to result from lethal parental excess caused by the union of a hypomethylated gamete from the hemizygote and a 2x gamete from the 4x parent. Conversely, the plump seeds are assumed to result from normally methylated gamete from the hemizygote and a 2x gamete from the 4x parent. Met1as plants appear therefore to produce both normally methylated and hypomethylated gametes. The plump seeds produce plants which segregate 1:1 for the Met1as gene. Presumably, the shrivelled seeds also segregate 1:1 for the Met1as gene. This data therefore demonstrates that the presence of the transgene in the endosperm is not responsible for the lethality phenotype associated with 2xMet1as-4x reciprocal crosses. If this were the case, seeds containing the Met1as gene would not be recovered among the plump, viable seed class.

Crosses Involving ddm Mutant Plants

Table 1 shows that crosses between wild type diploid and wild type tetraploid plants and plants homozygous for the ddm mutation have very similar outcomes to crosses involving plants containing the Met1as gene. The common feature of the ddm mutation and the action of the Met1as gene is that plants containing these genes have highly hypomethylated DNA. This shows that the interploidy cross effect produced in crosses involving gametes derived from ddm and Met1as plants is related to DNA hypomethylation.

The hemizygote data (Table 2) further suggests that the phenomenon involves hypomethylation of the gametes, presumably through the removal of genomic imprints.

TABLE 2

Outcomes of reciprocal crosses between Arabidopsis plants hemizygous for the Met1as gene and wild type 4x plants.

| | Mature Seed phenotypes (%)[1] | | Seed viability (%)[2] | | Proportion viable seeds carrying Met1as gene (%)[3] | Seed weight (μg)[4] | |
|---|---|---|---|---|---|---|---|
| | Plump seeds | Shrivelled seeds | Plump seeds | Shrivelled seeds | | Plump seeds | Shrivelled seeds |
| 4x-2xmetHET | 50 | 50 | 95–100 | 0 | 50 | 11 | 2 |
| 2xmetHET-4x | 50 | 50 | 95–100 | 0 | 50 | 23 | 8 |

Abbreviations:
2x, wild type diploid plant;
4x, wild type tetraploid plant;
2xmetHET, plant hemizygous for the Met1as gene
[1] scored by eye.
[2] determined by germination on soil of seed from mature pods.
[3] determined by PCR analysis on plants germinated from plump seeds.
[4] measured as described in Scott et al., 1998.

Example 2

Construction of Expression Cassettes that Restrict Gene Expression to Either the Gynoecium or the Stamen Example 1 demonstrates that uniparental demethylation can be used to control seed size. However, the increase in seed weight in the cross 2xmet1a/s-2x is smaller than for the corresponding interploidy cross (2x-4x). This may be due to the reduced fitness of the 35S Met1as female lines since demethylation is approximately constitutive. In order to reduce and eliminate this effect and to allow seed size changes to be obtained in a single plant it is necessary to restrict demethylation as much as possible to the germ line or gametes.

a. Designing a General Female-germ Line Specific Expression Vector

An expression vector based on the female-specific AGL5 promoter (Sessions et al (1998)) is constructed as described below. The nos polyA signal sequence is excised from pCaM- VNEO (Fromm et al (1986)) as a BamHI, HindIII fragment and cloned between the BamHI and HindIII sites of pBin19 (Bevan 1994) forming pNosterm-bin. A 2.2 kb AGL5 promoter is PCRed from *Arabidopsis* genomic DNA using the primers AGL5F and AGL5R which introduce an EcoRI and a KpnI site at the ends of the AGL5 PCR fragment.

```
                                              (SEQ ID NO: 1)
5' CCGAATTCTTCAAGCAAAAGAATCTTTGTGGGAG 3'    AGL5F
     EcoRI (SEW ID NO: 2)
5' CGGTACCTATAAGCCCTAGCTGAAGTATAAACAC 3'    AGL5R
     KpnI
```

Figure 4:
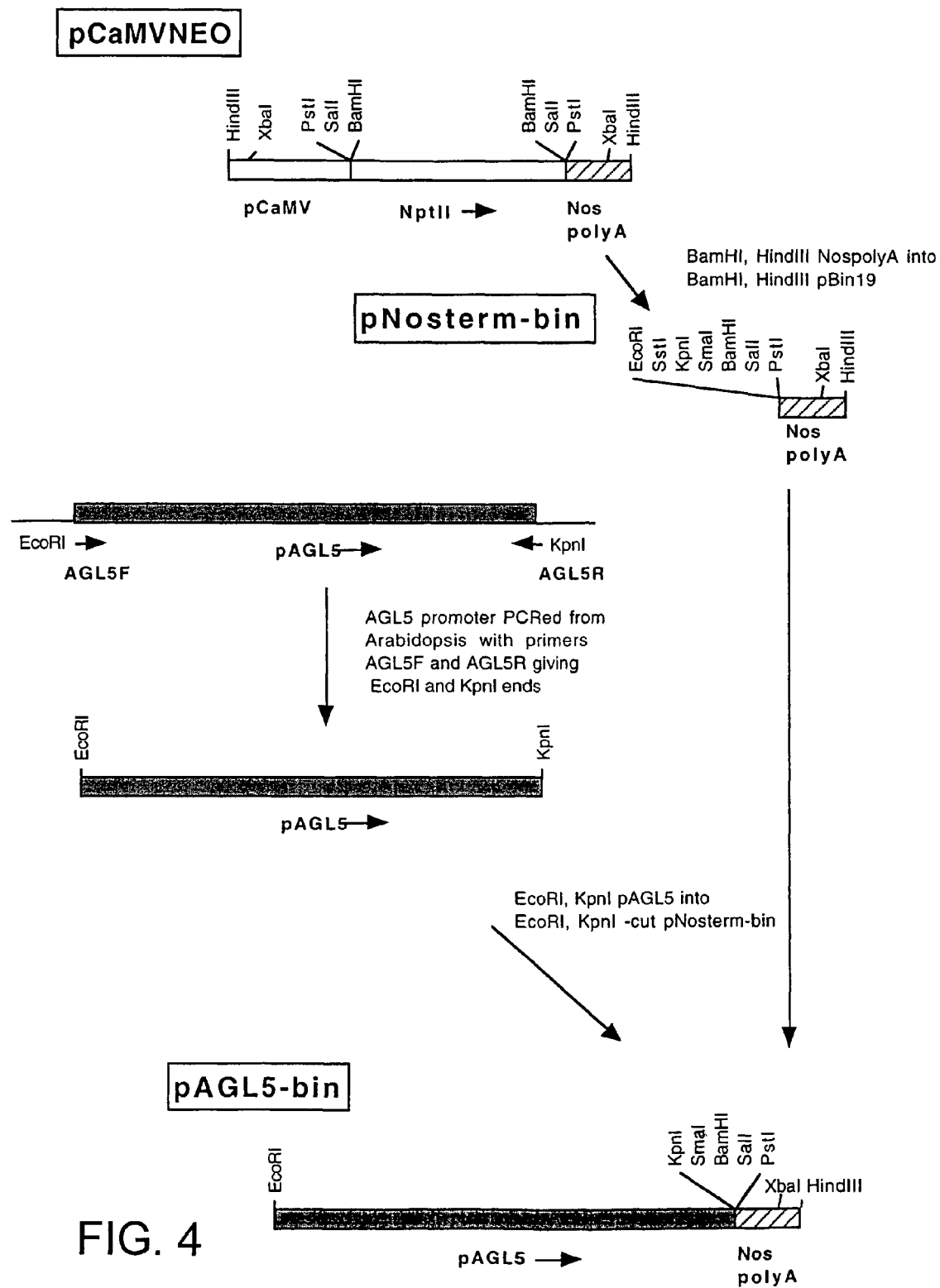
FIG. 4—Schematic diagram showing the method of construction of pAGL5-bin.

The AGL5 PCR fragment is cloned as an EcoRI, KpnI fragment between the EcoRI and KpnI sites of pNosterm-bin forming pAGL5-bin (FIG. 4).

b. Designing a General Male-germ Line Specific Expression Vector

An expression vector based on the male-specific AP3 promoter (Irish and Yamamoto (1995)) is constructed as described below. A 1.7 kb AP3 promoter is PCRed from *Arabidopsis* genomic DNA using the primers AP3F and AP3R which introduce an EcoRI and a KpnI site at the ends of the AP3 PCR fragment.

```
                                              (SEQ ID NO: 3)
5' CCGAATTCAAGCTTCTTAAGAATTATAGTAGCACTTG 3'  AP3F
     EcoRI (SEQ ID NO: 4)
5' GGGTACCTTCTCTCTTTGTTTAATCTTTTTGTTGAAGAG 3' AP3R
     KpnI
```

Figure 5:
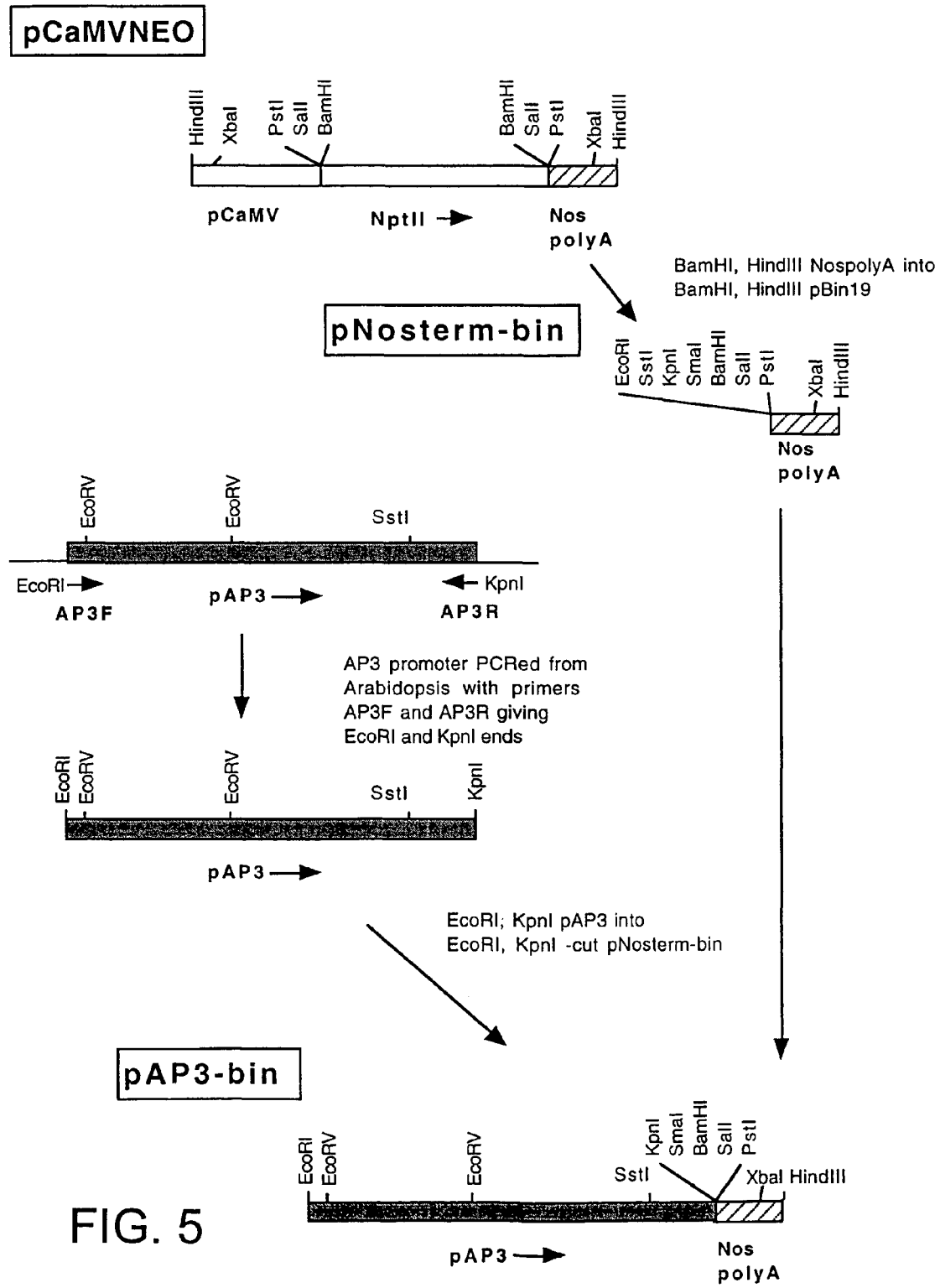
FIG. 5—Schematic diagram showing the method of construction of pAP3-bin.

The AP3 PCR fragment is cloned as an EcoRI, KpnI fragment between the EcoRI and KpnI sites of pNosterm-bin forming pAP3-bin (FIG. 5).

Example 3

Construction of Chimaeric Gene Fusions Between the Female (Example 2a) and Male (Example 2b) Germ-line Specific Cassettes and the Met1 Antisense Gene Expression of the MET1 gene can be reduced in the female or male germ lines by employing techniques known in the art. For example MET1 down-regulation can be achieved by expressing antisense MET1 or antisense MET1 fragments or sense MET1 or partial sense MET1 or ribozymes directed against MET1 or combinations of the preceding, from promoters expressed in the required germ-line. Below is an example of an antisense MET1 approach.

a) The Construction of a Female Germ-line Specific Met1as Gene

The MET1 CDNA is 4.7 kb long and is isolated by RT-PCR from *Arabidopsis* CDNA using the primers MET1F and MET1R.

```
                                              (SEQ ID NO: 5)
5' ACTCGAGATTTTGAAAATGGTGGAAAATGGGGC 3'      MET1F
     XhoI (SEQ ID NO: 6)
5' ACCCGGGTGGTTATCTAGGGTTGGTGTTGAGGAG 3'     MET1R
     SmaI
```

Figure 6:
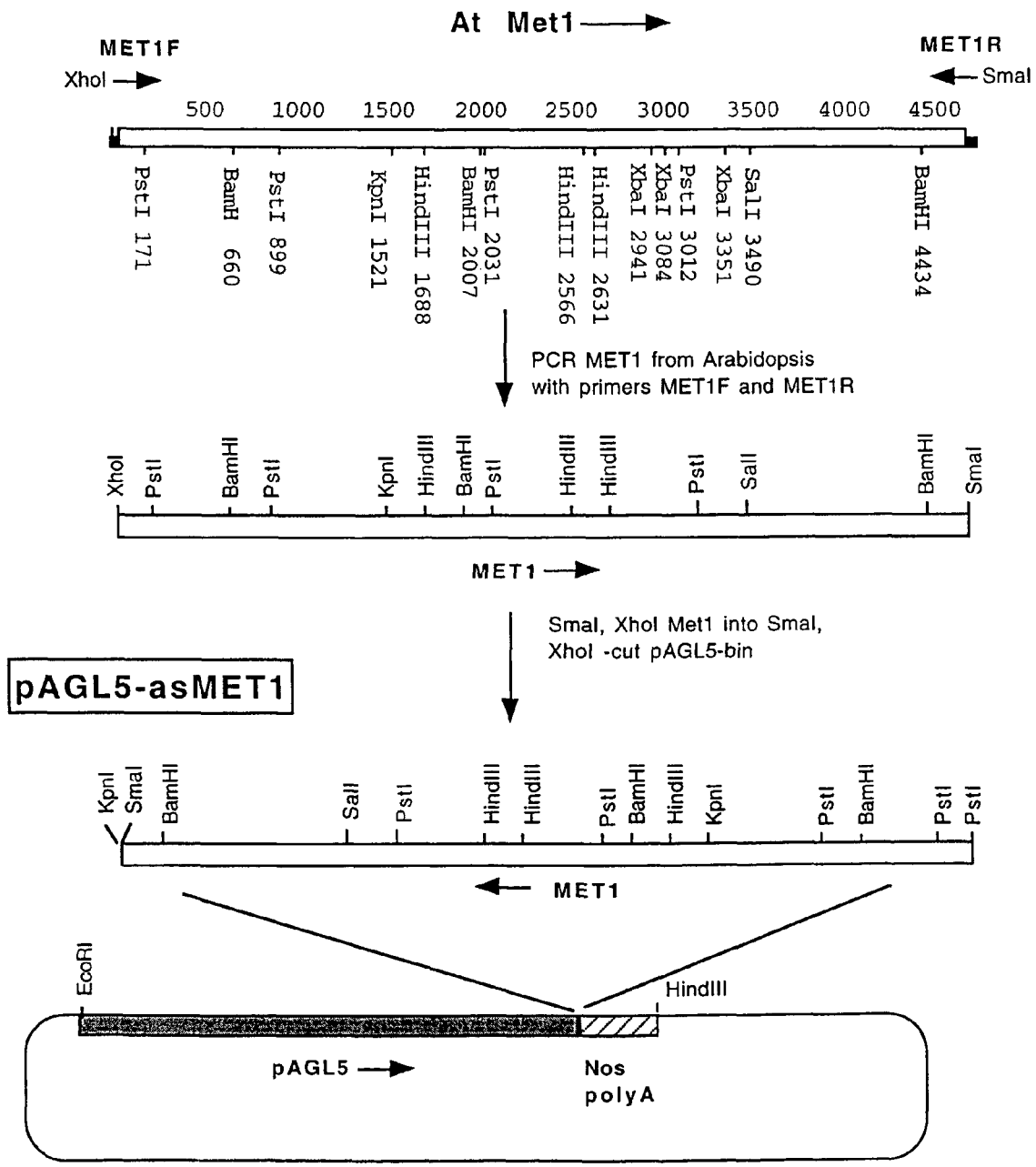
FIG. 6—Schematic diagram showing the method of construction of pAGL5-asMET1

The resulting MET1 PCR fragment is then cloned as a SmaI, XhoI fragment between the SmaI and SalI sites of pAGL5-bin forming pAGL5-as MET1 (FIG. 6).

b) The Construction of a Male Germ-line Specific Met1as Gene

Figure 7:
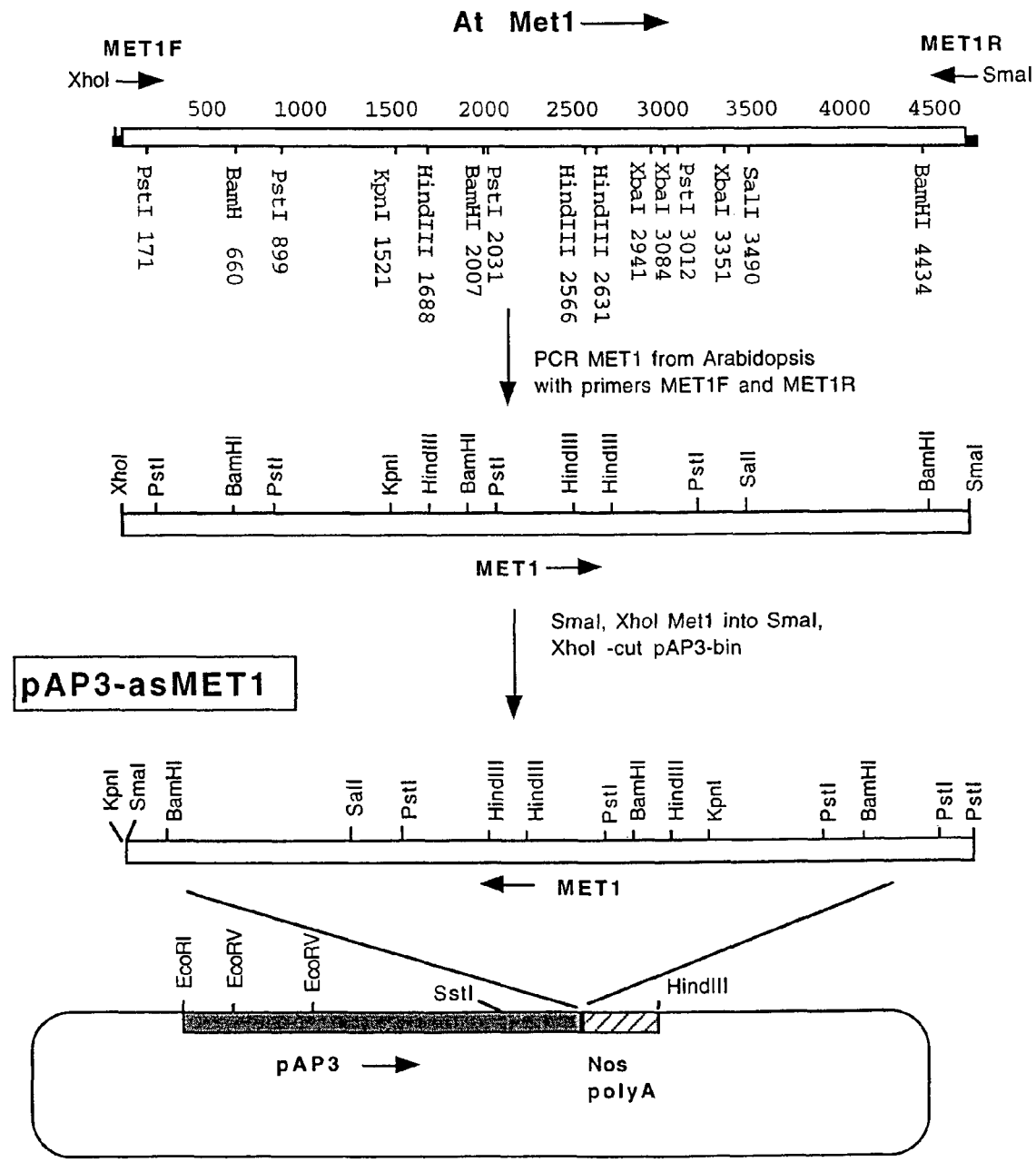
FIG. 7—Schematic diagram showing the method of construction of pAP3-asMET1

The MET1 PCR fragment is cloned as a SmaI, XhoI fragment between the SmaI and SalI sites of pAP3-bin forming pAP3-as MET1 (FIG. 7).

Example 4

Introduction of Female and Male Germ-line Specific Demethylating Genes Into Transgenic Plants Chimaeric genes were introduced via *Agrobacterium*-mediated transformation into wild type diploid *Arabidopsis* using well known techniques.

a) pAGL5Met1as

Transgenic *Arabidopsis* plants containing the pAGL5Met1as gene were vegetatively normal and produced flowers with the normal complement of floral organs. *Arabidopsis* containing pAGL5Met1as were pollinated with pollen from wild-type diploid plants or allowed to self pollinate. Endosperm development in the resulting seeds was monitored by confocal microscopy (Scott et al., 1998) and seed weights were measured at maturity. In both cases, endosperms showed a paternal excess phenotype (average maximum endosperm size=800 nuclei, delayed cellularisation (+1-2 days relative to 2x-2x crosses wild type) and chalazal endosperm hyperplasia) similar to that obtained in 2x-4x crosses between wild type plants (Table 1).

The mean weight of mature seed collected from pAGL5Met1as plants was 40 μg, compared with a mean of 22 μg for 2x-2x seed. This represents an increase in seed weight compared to the mean of the 2x-2x.

The germination frequency was comparable to that of seed from 2x-2x wild type crosses—95-100%.

The outcomes of the crosses were variable and depended on the particular transgenic plant.

The pAGL5Met1as gene could be transformed into other crop species such as *B. napus* and *Zea mays*, leading to an increase in seed size and seed quality in the transgenic plants. In this case it is most preferable to use MET1 and AGL5 orthologous sequences from *B. napus* and *Zea mays*.

b) pAP3Met1as

A proportion of transgenic *Arabidopsis* plants containing the pAP3Met1as gene were vegetatively normal and produced flowers with the normal complement of floral organs.

*Arabidopsis* containing pAP3Met1as were pollinated with pollen from wild-type diploid plants or allowed to self pollinate. Endosperm development in the resulting seeds was monitored by confocal microscopy (Scott et al., 1998) and seed weights were measured at maturity. In both cases, endosperms showed a moderate maternal excess phenotype increased peripheral endosperm cell number, precocious cellularisation and chalazal endosperm hypoplasia qualitatively similar to that obtained in 4x-2x crosses between wild type plants (Table 1).

The mean weight of mature seed collected from pAP3Met1as plants is less than that of 2x-2x seed.

The germination frequency was comparable to that of seed from 2x-2x wild type crosses—about 95-100%.

The pAP3Met1as gene could be transformed into other crop species such as *B.napus* and *Zea mays*, leading to an decrease in seed size in the transgenic plants. In this case it is most preferable to use MET1 and AP3 orthologous sequences from *B. napus* and *Z. mays*.

Example 5

Promoting Interspecific Hybridisation

Tetraploid *Arabidopsis thaliana* were obtained by the method, known to those skilled in the Art, of Colchicine doubling of a diploid plant.

Figure 8:
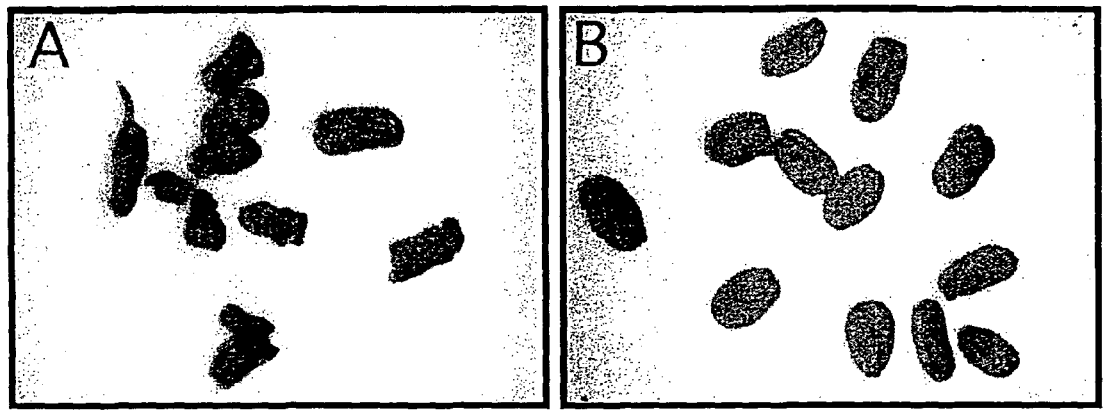
FIG. 8—Seed production following inter-specific crosses between *Arabidopsis thaliana* and *Arabidopsis lyrata*. Light micrographs of seeds taken from mature seed pods. A, 4x *A. thaliana*X*A. lyrata*; note seeds are shrivelled (see Table 3 for germination data). B, 4x *A. thaliana* Met1a/s X *A. lyrata* (4x *A. thaliana* Met1a/s=hypomethylated tetraploid line expressing Met1a/s gene); note that seeds are plump (see Table 3 for germination data). See text for full details.

Cross pollination between tetraploid *Arabidopsis thaliana* (4x *A.thaliana*) and *Arabidopsis lyrata*, results in 100% shrivelled seed (FIG. 8A) that fail to germinate (Table 3). Abortion is due to endosperm failure resulting from lethal relative genomic imbalance (FIG. 8B). This post-fertilisation hybridisation barrier is overcome by introducing the Met1a/s gene into the 4x *A. thaliana* parent; the resulting plants produce hypomethylated gametes. Cross pollination between a 4x *A.thaliana* Met1 a/s seed parent and *Arabidopsis lyrata*, results in plump seed (FIG. 8B) which germinate at high frequency (Table 3). This illustrates the utility of hypomethylation, as conditioned by the Met1a/s gene in this example, to promote inter-specific hybridisation between two plants that do not normally form viable hybrids.

pAGL5Met1as and pAP3Met1as were transformed into *Brassica campestris* and *Brassica oleraceae* via standard methods. Reciprocal crosses between the transgenic individuals of the two species yield plump seeds which germinate to give hybrid plants. Crosses between wild type individuals of the two species result in shrivelled seeds which fail to germinate. Hence the two transgenes overcome the normal barrier to interspecific hybridisation. The same genes could be used in other species or varieties to promote hybridisation.

Table 3 Relaxing genomic imprinting through hypomethylation can promote or prevent hybrid formation

TABLE 3

Relaxing genomic imprinting through hypomethylation can promote or prevent hybrid formation

| Cross | Outcome of Cross | | |
|---|---|---|---|
| | Endosperm phenotype | Seed viability (% germination) | Hybrids formed? |
| 4x*A. thaliana* X *A. lyrata* | ME | 0 | NO |
| 4x*A. thaliana*-Met1a/s X *A. lyrata* | Moderate PE | 95-100 | YES |
| 4x*A. thaliana* X *C. arenosa* | Lethal PE | 95-100 | YES |
| 2x*A. thaliana* X *C. arenosa* | Lethal PE | 0 | NO |
| 4x*A. thaliana*-Met1a/s X *C. arenosa* | Lethal PE | 0 | NO |

PE, paternal excess as described in Scott et al, 1998.
ME, maternal excess as described in Scott et al, 1998.

Example 6

Preventing Interspecific Hybridisation

Figure 9:
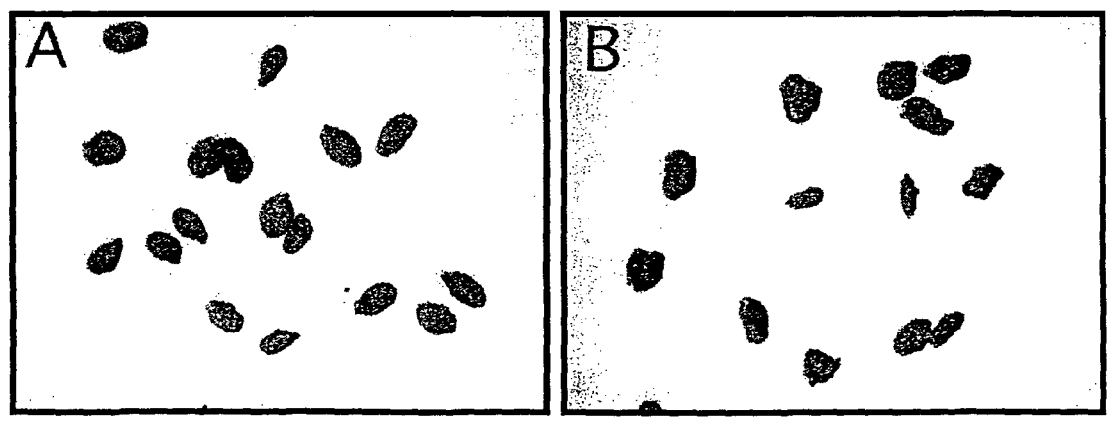
FIG. 9—Seed production following inter-specific crosses between *Arabidopsis thaliana* and *Cardaminopsiss arenosa*. Light micrographs of seeds taken from mature pods. A, 4x *A. thaliana*X *C. arenosa*; note seeds are plump (see Table 3 for germination data). B, 4x *A. thaliana* Met1a/s X *C. arenosa*; note seeds are shrivelled (see Table 3 for germination data).

Cross pollination between tetraploid *Arabidopsis thaliana* (4x *A.thaliana*) and *Cardaminopsis arenosa*, results in 100% plump seed (FIG. 9A) that germinates at high frequency (Table 3). The hybrid is a synthetic version of a naturally occurring hybrid between these two species—*Arabidopsis suesica* (Chen et al., 1998). Cross pollination between diploid *Arabidopsis thaliana* (2x *A.thaliana*) and *C. arenosa*, results in 100% shrivelled seed that fails to germinate (Table 3). Accordingly, *C. arenosa* can be said to have a genomic strength that is sufficiently high to cause seed abortion when combined with 2x *A. thaliana*, but not when combined with 4x *A. thaliana*. To demonstrate that hypomethylation can prevent cross bybridisation between *A. thaliana* and *C. arenosa* the Met1a/s gene was introduced into 4x *A. thaliana*, and this plant used as seed parent in a cross to *C. arenosa*. Seed from such a cross is 100% shrivelled (FIG. 9B) and fails to germinate (Table 3). The same gene could be used in other species or varieties to prevent the production of viable hybrid seed.

Example 7

Maternal Hypomethylation Promotes Autonomous Endosperm Development

Figure 12:
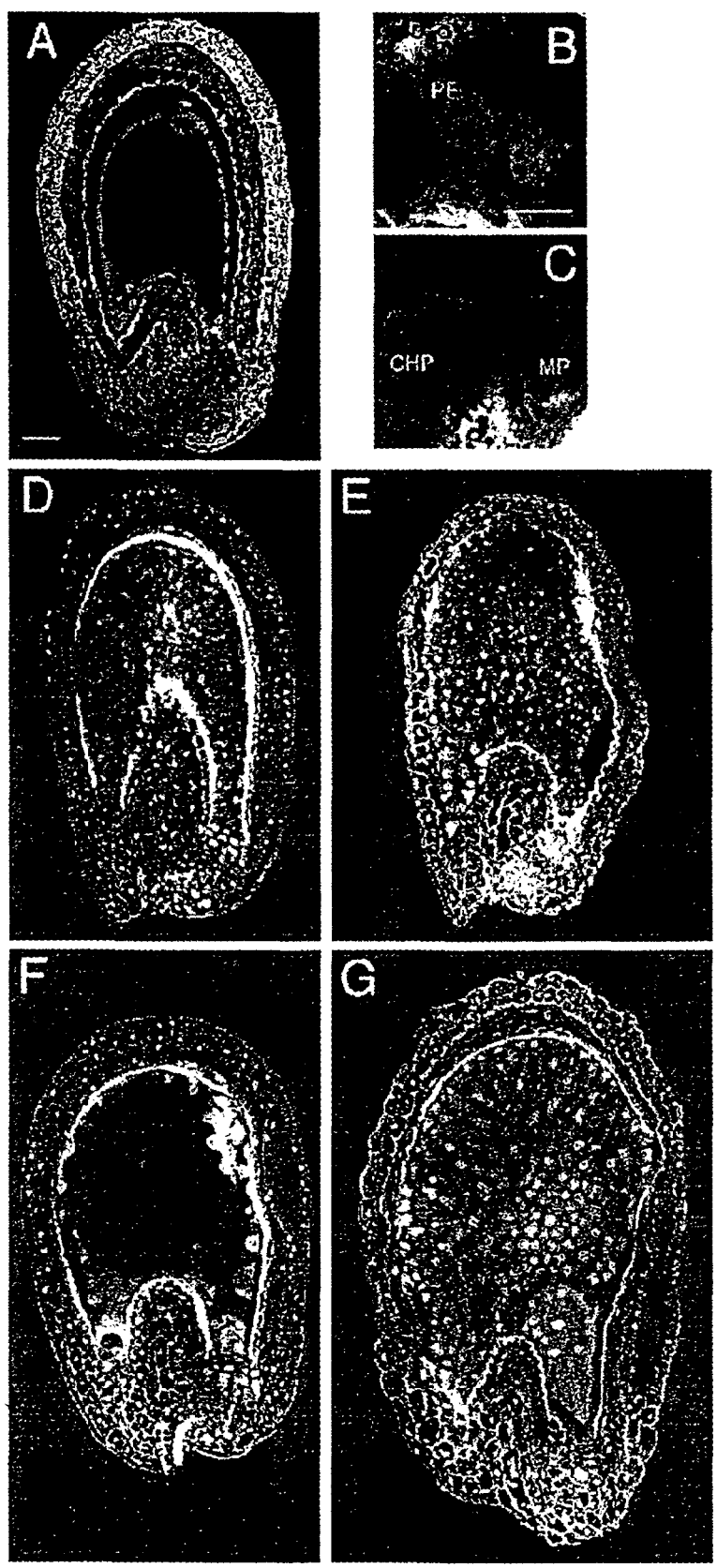
FIG. 12—Autonomous endosperm development in unfertilised seeds of *Arabidopsis thaliana*. Confocal micrographs of fertilization-independent seeds produced by emasculated fie-1/FIE heterozygotes with normal and reduced methylation. (A-C) Seed-like structure from a plant with normal methylation. (A) Optical section showing peripheral endosperm but no well differentiated chalazal endosperm. Bar50 µm. (B) Clustered endosperm nuclei at periphery. (PE, peripheral endosperm.) Bar=50 µm. (C) Endosperm at micropylar (MP) and chalazal (CHP) poles. (D-G) Seed-like structures from fie-1/FIE; MET1a/s plants. (D, E) Type 1 seed-like structures at 7 (D) and 10 (E) days after emasculation (DAE). In these the endosperm cellularizes and fills the interior of the embryo sac. (F, G) Type 2 seed-like structures at 7 (F) and 10 (G) DAE. These produce micropylar and chalazal in addition to peripheral endosperm.

In the absence of fertilization, *Arabidopsis* plants heterozygous for the fie-1 mutation (fie/FIE) produce seeds with partial endosperm development (Ohad et al., 1996; 1999; see also Table 4 and FIG. 12 A-C). These 'autonomous' endosperms consist of a severely reduced number of endosperm nuclei (compared to wild type controls) and the endosperm fails to undergo cellularization. The seed collapses and becomes shriveled at maturity (Table 4). Consequently, the fie mutation conditions only limited endosperm development restricting its utility in the production of autonomous apomictic seed crops or embryoless seed crops. Endosperms produced in plants carrying the fis1/mea and fis2 mutations are very similar to those of fie/FIE plants, and hence the utility of these genes is also restricted.

Since "fie" endosperms do not contain a paternal genomic contribution one hypothesis is that proper development of the endosperm requires the expression of paternally derived genes that are subject to maternal imprinting.

Figure 10:
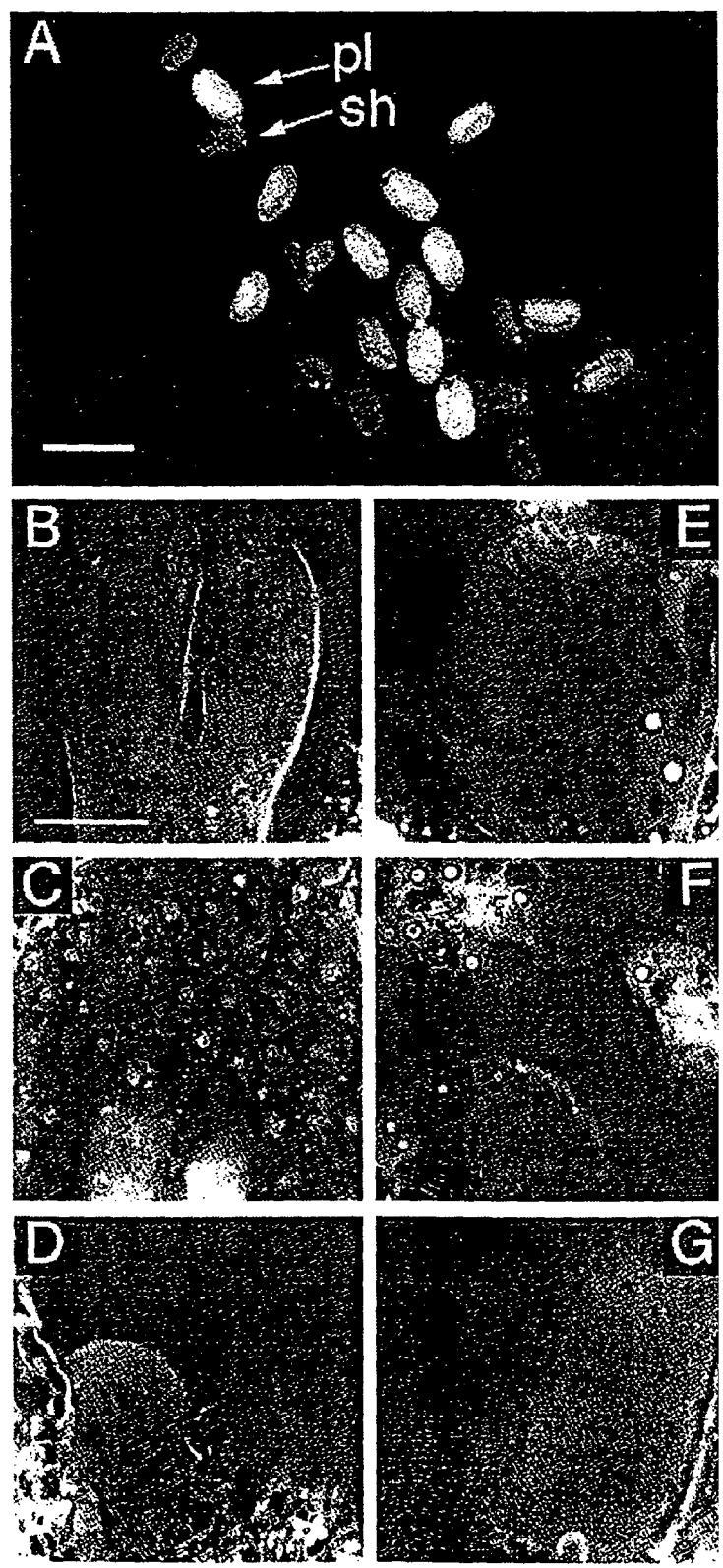
FIG. 10—Seeds from a fie-1/FIE X FIE/FIE cross. (A) Light micrograph showing the two classes of seeds, plump (pl) and shrivelled (sh). (Bar=5 mm). (B-G) Confocal micrographs of normal (B-D) and aborting (E-G) seeds at 8 DAP, centred on micropylar (B, E), central (C, F), and chalazal (D, G) regions of the embryo sac. The endosperm in (E-G) is overgrown and has not cellularized. Bar=50 µm.

When plants heterozygous for the fie mutation are pollinated with wild type pollen from a 2x wild type plant the ovules carrying the fie allele develop into seeds that abort at heart/torpedo stage, while ovules carrying the wild type FIE allele develop normally (Ohad et al., 1996; 1999; Table 4 and FIG. 10). The aborted seeds express a strong paternal excess phenotype (Table 4; FIG. 10), despite containing only a single paternal contribution. This suggests that a complex situation with respect to imprinting applies within fertilised and unfertilised fie endosperms. One hypothesis is that the fie mutation lifts imprinting from a proportion of genes normally subject to maternal imprinting: the introduction of a additional paternal genome following fertilisation generates an effective lethal paternal excess such as encountered in a 2x-6x wild type cross (Table 1). The failure of fie endosperms to development normally in the absence of fertilisation is also accounted for by this hypothesis, since not all maternally imprinted genes may be derepressed.

Figure 11:
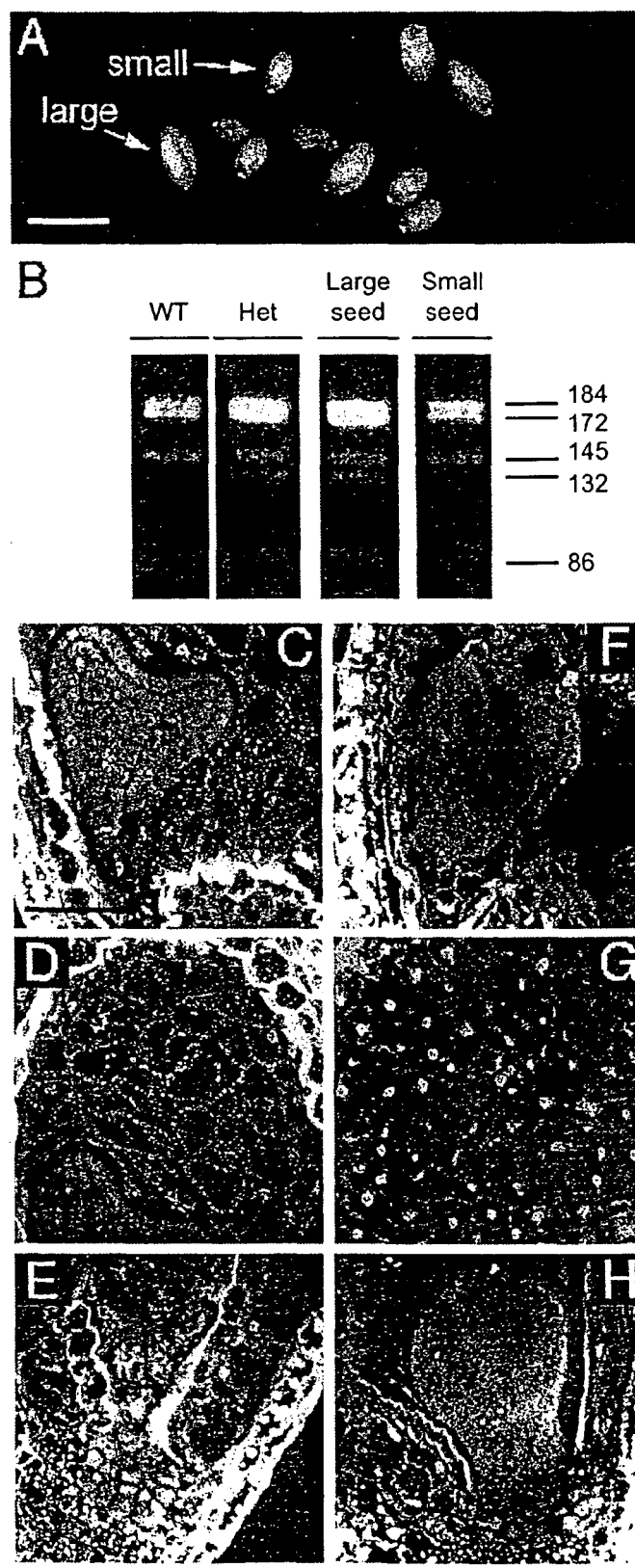
FIG. 11—Seeds from a [fie-1/FIE X FIE/FIE; MET1a/s/ MET1a/s] cross. (A) Light micrograph showing the two classes of seeds. All seeds are plump, indicating that a pollen parent hypomethylated by the MET1a/s transgene can rescue fie-1 mutant seeds. Bar=5 mm. (B) Identification of the fie-1 and FIE alleles by PCR and restriction enzyme analysis . The wild type FIE allele produces four bands (lane 1, WT) while fie-1/FIE heterozygotes (lane 2, Het) have an extra band. All large seeds scored had the heterozygous pattern (lane 3) while all small seeds were wild type (lane 4). (C-H) Confocal micrographs of seeds at 8 DAP. The seed in (C-E) has a similar phenotype to seeds from interploidy crosses generating maternal genomic excess, while (F-H) shows characteristics of paternal excess (see text, and Scott et al., 1998). Bar=50 µm.

Since gametes derived from hypomethylated plants (Met1as and ddm) appear to have no or highly attenuated imprinting, and therefore act in part as gametes of the opposite sex in endosperms, we hypothesised that such gametes in combination with the fie mutation would promote complete endosperm development. In the first experiment, we used pollen from a Met1as plant [FIE/FIE; METI a/s/METI a/s] to pollinate a FIE/fie heterozygote [fie/FIE; METI a/s/METI a/s] and found most seeds produced were plump and viable (Table 4; FIG. 11). The seeds segregate 1:1 for the FIE/FIE:

FIE/fie genotypes, showing that the fie allele is transmissible through the seed parent in this cross. The FIEFIE seeds display a maternal excess phenotype as expected—endosperm under-development (Table 5) and a reduced seed weight (Table 4), whilst the Fiefie seeds display a moderate paternal excess phenotype (Table 5), similar to that observed in a 2xX4x cross between wild type *A. thaliana* plants. When wild type pollen from a diploid plant is used in this cross, the resulting seeds segregate 1:1 for plump/viable:shrivelled/inviable and the ovules containing the fie mutation produce inviable seed since the plump seeds all contain the wild type FIE allele (Table 4; FIG. 10). The abortive seeds display a paternal excess phenotype similar to that observed in a 2x-6x cross between wild type *A. thaliana* plants (FIGS. 3 and 10; Table 5). Therefore, paternal gametes from Met1as plants appear to rescue fie containing seeds from lethality by reducing the magnitude of the paternal excess phenotype. This supports the hypothesis as outlined above.

In the second experiment we combined the fie mutation and the Met1as gene into the same individual (see Table 4 and FIG. 12). When these plants were emasculated and left unpollinated 50% of the ovules underwent autonomous endosperm development as expected for ovules carrying the fie mutation. Confocal microscopy showed that these seeds contain well developed, cellularised endosperms (FIG. 12), with between 500-700 peripheral nuclei, a cellularisation time of 5-8 days and a volume of chalazal endosperm between 0.01 and 10X that of a seed produced in a 2x-2x cross. The mature seeds were shrivelled, but weighed 15 μg. In contrast, developing ovules of emasculated and unpollinated Fie/fie plants contain very under-developed endosperm that do not cellularise (FIG. 12). These seeds contain about 200 peripheral endosperm nuclei and no recognizable chalazal endosperm. The mature seeds were shrivelled and weighed 5 μg. The production of an endosperm that has the main features of a wild type endosperm (numerous peripheral endosperm nuclei, cellularisation, and a chalazal endosperm) in plants containing both the fie mutation and the Met1as gene shows that the lifting or attenuation of imprinting within the maternal gamete as conditioned by the Met1as gene is sufficient to relieve the developmental block encountered in unpollinated fie ovules. This greatly extends the utility of the autonomous endosperm mutants (fis1, fis2, fis3, and fie).

TABLE 4

Enhancement of endosperm development in fie mutant seeds by hypomethylation

| | Mature seed phenotypes (%)[1] | | Seed viability[2] | | Seed weight μg)[3] | | Extent of endosperm development (%)[4] | |
|---|---|---|---|---|---|---|---|---|
| | Plump seeds | Shrivelled seeds | Plump seeds | Shrivelled seeds | Plump seeds | Shrivelled Seeds | Complete | Partial |
| FIE/fie X 2x | 50 | 50 | 95-100 | 0 | 25 | 15 | 50 | 50[5] |
| FIE/fie X 2xmet | 100 | 0 | 95-100 | NA | 50% = 15 50% = 30 | NA | 100 | 0 |
| FIE/fie emasculate | 0 | 100 | NA | 0 | NA | 5 | 0 | 100[6] |
| FIE/fie: 2xmetHET emasculate | 0 | 100 | NA | 0 | NA | 20 | 100 | 0 |

NA, not applicable;
FIE/fie, plant heterozygous for the fie mutation;
2x, wild type diploid plant;
2xmet, plant homozygous for the Met1as gene;
FIE/fie, 2xmetHET FIE/fie heterozygous line containing a single Met1as antisense gene (introduced by crossing FIE/fie and Met1as and recovering appropriate genotype in the F1).
[1]scored by eye.
[2]determined by germination on soil.
[3]measured as described in Scott et al., 1998.
[4]determined by confocal microscopy as described in Scott et al, 1998; complete corresponds to normal development as occurs in control crosses, partial refers to abnormal development such as a failure to cellularise or develop chalazal endosperm.
[5]resembles lethal paternal excess as occurs in 2x-6x crosses
[6]as described by Ohad et al, 1999.

TABLE 5

Endosperm development in crosses involving fie, met1a/s and wild type plants.

| | fie/FIE X FIE/FIEmet/met | | fie/FIE X FIE/FIE | |
|---|---|---|---|---|
| | FIE/FIE seeds | fie/FIE seeds | FIE/FIE seeds | fie/FIE seeds |
| Maximum number of P.E nuclei | 192 | 637 | 447 | 408 |
| Timing of endosperm cellularisation | 3-4 DAP | 7-8 DAP | 5-6 DAP | >10 DAP |
| Size of chalazal Endosperm[1] | 0.05-0.1X | 3-4X | 1X | 10-15X |

[1]area of maximum cross-section relative to wild type

Example 8

Production of Plants that Combine the fie Mutation and the Female Germ-line Specific Demethylating Gene, AGL5Met1a Plants heterozygous for the fie mutation and hemizygous for the pAGL5Met1as gene were generated by making crosses between FIE/fie plants as pollen parent and plants homozygous for the pAGL5Met1as gene as seed parent. These plants were vegetatively normal and produced normal flowers. When emasculated 50% of the ovules initiated seed development without fertilisation. Confocal microscopy showed that endosperm development was extensive, resulting in a large (500-700 nuclei) cellularised endosperm.

The pAGL5Met1as gene could be introduced into crop species, such as *B.napus* and *Zea mays* in which expression of the FIE gene, or any of the genes that condition autonomous endosperm development, is suppressed or absent through mutation or the use of transgenic technologies, to produce promote apomixis or embryoless (pseudoapomictic) seed. Preferably the pAGL5Met1as construct contains *B.napus* or *Z.mays* MET1 and AGL5 orthologous sequences

EXAMPLE 9

The Use of FIE Down-regulation to Paternalise Female Gametes (Polar Nuclei)—to Increase Endosperm Size and Seed Weight When plants heterozygous for the fie mutation (Ohad et al., 1996; 1999) are pollinated with pollen from a 2x wild type plant the ovules carrying the fie allele develop into seeds that abort at heart/torpedo stage, while ovules carrying the wild type FIE allele develop normally (Ohad et al, 1996; 1999; Table 4 and FIG. 10). The aborted seeds express a strong paternal excess phenotype (Table 4; FIG. 10), despite containing only a single paternal contribution. This suggests that a complex situation with respect to imprinting applies within fertilised and unfertilised fie endosperms. This is explained by proposing that the fie mutation lifts imprinting from genes normally subject to maternal imprinting (the maternal gametes are thus strongly paternalised): the introduction of a additional paternal genome following fertilisation generates an effective lethal paternal excess (2maternal;3paternal) such as encountered in a 2x-6x wild type cross (2m:3p) (Table 1).

Since gametes derived from hypomethylated plants (Met1as and ddm) appear to have no or highly attenuated imprinting, and therefore act in part as gametes of the opposite sex in endosperms, such gametes in combination with the fie mutation could promote complete endosperm development. In the first experiment, pollen from a Met1as plant [FIE/FIE; METI als/METI a/s] is used to pollinate a FIE/fie heterozygote [fie/FIE; METI a/s/METI a/s] and most seeds produced were plump and viable (Table 4; FIG. 11). The seeds segregate 1:1 for the FIE/FIE:FIE/fie genotypes, showing that the fie allele is transmissible through the seed parent in this cross. The FIEFIE seeds display a maternal excess phenotype as expected—endosperm under-development (Table 5) and a reduced seed weight (Table 4), whilst the Fiefie seeds display a moderate paternal excess phenotype (Table 5), similar to that observed in a 2xX4x cross between wild type *A. thaliana* plants. When wild type pollen from a diploid plant is used in this cross, the resulting seed segregate 1:1 for plump/viable:shrivelled/inviable and the ovules containing the fie mutation produce inviable seed since the plump seeds all contain the wild type FIE allele (Table 4; FIG. 10). The abortive seeds display a paternal excess phenotype similar to that observed in a 2x-6x cross between wild type *A. thaliana* plants (FIGS. 3 and 10; Table 5). Therefore, paternal gametes from Met1as plants appear to rescue fie containing seeds from lethality by reducing the magnitude of the paternal excess phenotype. As the fie mutation appears to cause strong paternalisation of the maternal gametes (polar nuclei), wild-type FIE may participate directly in maternal imprinting (as part of the imprinting complex).

The paternalisation of the polar nuclei by the fie mutation is more extensive than that achieved by met1a/s since a fieX2x cross results in lethal paternal excess (Table 4; FIG. 10), but a met1a/s X2x cross produces viable paternal excess, with increased endosperm size and seed weight (Table 1). Thus the degree of paternalisation of the polar nuclei determines the outcome of crosses with pollen from diploid wild type plants: moderate paternalisation (e.g MetIa/s) produces a large viable seed due to moderate paternal excess in the endosperm, whereas strong paternalisation (e.g fie null mutation) results in seed lethality due to excessive paternal excess in the endosperm. Modulating FIE expression may have application in manipulating endosperm size and seed weight. The fie mutation used is a null allele (fie-1; Ohad et al, 1999)—no functional FIE protein is produced, resulting in strong paternalisation of the polar nuclei, and seed lethality in crosses with wild type pollen from a diploid plant. Reducing, but not eliminating the expression of FIE results in moderate paternalisation of the polar nuclei; the exact level of paternalisation being directly related to the amount of FIE protein expression during female gametogenesis. Reduction in FIE expression can be achieved using a number of well known methods such as antisense RNA expression against the sense FIE RNA transcript. Incremental reduction in FIE expression, by making use of for example different, more or less effective, anti-sense lines, identifies a level of FIE expression that is optimal for producing viable seeds with a maximally increased endosperm size and seed weight.

Suitable anti-sense genes would comprise the FIE promoter driving transcription of the anti-sense FIE transcribed region. Other genes suitable to reduce the levels of FIE expression and deliver levels of paternalisation of polar nuclei intermediate between a FIE null allele and the wild type FIE allele include genes encoding fragments of the FIE protein which recognise and bind to imprinted genes, but are ineffective in promoting their non-expression in the endosperm (e.g. because the repressive complex cannot form or cannot be maintained).

REFERENCES

Angenent, G. C. et al (1995). A novel class of MADS box genes is involved in ovule development in *Petunia*. Plant Cell 7, 1569-1582.

Alexander, H M. and Wulff, R D. (1985). Experimental ecological genetics in *Plantago* X. The effects of maternal temperature on seed and seedling characters in *P. lanceolata*. Journal of Ecology 73, 271-282.

Bender, J. and Fink, G R. (1995). Epigenetic control of an endogenous gene family is revealed by a novel blue florescent mutant of *Arabidopsis* Cell 83, 725-734.

Bevan (1994). Binary *Agrobacterium* vectors for plant transformation. Nucleic Acids Research 12, 8711-8721.

Bhattacharya, S. K., Ramchandani, S., Cervoni, N. and Szyf, M. (1999) A mammalian protein with specific demethylase activity for mCpG dna. Nature 397, 579-583

Brink, R. A. and Cooper, D. C. (1947). The endosperm in seed development. Bot. Rev. 13, 423-541.

Brutnell, T. P. and Dellaporta, S. L. (1994) Somatic inactivation and reactivation of Ac associated with changes in cytosine methylation and transposase expression. Genetics 138, 213-225

Chaudhuri, S. and Messing, J, (1994). Allele-specific parental imprinting of dzr1, a post transcriptional reguilator of zein accumulation. Proc. Natl. Acd. Sci USA 91, 4867-4871.

Chaudhury, A. et al. (1997) Fertilization-independent seed development in *Arabidopsis thaliana*. Proc. Natl. Acad. Sci USA 94: 4223-4228

Chen, Z. J., Comai, L., Pikaard, C. (1998). Gene dosage and stochastic effects determine the severity and direction of uniparental ribosomal RNA silencing (nuclear dominance) in *Arabidopsis* allopolyploids. Proc. Natl. Acd. Sci USA 95, 14891-14896.

Colombo, L. et al (1995). The *Petunia* MADS box genes is involved in ovule identity. Plant Cell 7, 1859-1868.

Duvick, D. N. (1992) Genetic contributions to advances in yield of United States maize. Maydica 37, 69-79

Ehlenfeldt, M K. and Ortiz, R. (1995). Evidence on the nature and origins of endosperm dosage requirements in Solanum and other angiopserm genera. Sexual Plant Reproduction 8, 189-196.

Finnegan, E. J., Peacock, W J and Dennis, E S (1996). Reduced DNA methylation in *Arabidopsis thaliana* results in abnormal plant development. Proc. Natl. Acad. Sci. USA 93, 8449-8454.

Foster, G. D., Robinson, S. W., Blundell, R. P., Roberts, M. R., Hodge, R., Draper, J. and Scott, R. J. (1992). A *Brassica napus* mRNA encoding a protein homologous to phospholipid transfer proteins, is expressed specifically in the tapetum and developing microspores. Plant Science 84, 187-192.

Fromm M E, Taylor L P and Walbot V. (1985). Stable transformation of maize after gene transfer by electroporation. Nature 319, 791-793.

Giroux M J, Shaw J, Barry G, Cobb B G, Greene T, Okita T and Hannah L C (1996). A single mutation that increases maize seed weight. Proc Natl Acad Sci USA 11, 5824-9.

Goto, K., and Meyerowitz, E M. (1994). Function and regulation of the *Arabidopsis* floral homeotic gene PISTILLATA. Genes and Devel. 8, 1548-1560.

Grossniklaus, U., VielleCalzada, J. P., Hoeppner, M. A. and Gagliano, W. B. (1998) Maternal control of embryogenesis by medea, a Polycomb group gene in *Arabidopsis*. Science 280, 446-450

Gruenbaum, Y., Naveh-Many, T., Cedar, H. and Razin, A. (1981) Sequence specificity of methylation in higher plant DNA. Nature 292, 860-862

Guberac, V., Martinic, J. and Maric, S. (1998). Influence of seed size on germinability, germ length, root length and grain yield in spring oat. Bodenkultur 49, 13-18.

Haig, D. and Westoby, M. (1991). Genomic imprinting in endosperm: its effect on seed development in crosses between species, and different ploidies of the same species, and its implications for the evolution of apomixis. Philosphical transactions of the Royal; Society London 333, 1-13.

Hannah, L C. and Greene, T W. (1998). Maize seed weight is dependent on the amount of endosperm ADP-glucose pyrophosphorylase. Journal of Plant Physiology 152, 649-652.

Irish, V. F. and Yamamoto, Y. T. (1995) Conservation of floral homeotic gene function between *Arabidopsis* and *Antirrhinum*. Plant Cell 7(10), 1635-1644

Jack, T., Brockman, L L., and Meyerowitz, E M. (1992). The homeotic gene Apetala3 of *Arabidopsis thaliana* encodes a MADS box and is expressed in petals and stamens. Cell 68, 683-697.

Jones, P. L.; Veenstra, G. J. C.; Wade, P. A.; Vernaak,. D.; Kass, S. U.; Landsberger, N., Strouboulis, J. and Wolffe, A. P. (1998) Methylated DNA and MeCP2 recruit histone deacetylase to repress transcription. Nature Genet. 19, 187-191

Kakutani, T. Jeddeloh, J. A. and Richards, E. J. (1995). Characterisation of an *Arabidospis thaliana* DNA hypomethylation mutant. Nucleic Acids Res. 23, 130-137.

Kakutani, T., Jeddeloh, J. A., Flowers, S K., Munakatas, K. and Richards, E. J. (1995). Developmental abnormalities and epimutations associated with DNA hypomethylation mutants. Proc. Natl. Acad. Sci. USA 93, 12406-12411.

Kass, S. U.; Landsberger, N. and Wolffe, A. P. (1997) DNA methylation directs a time-dependent repression of transcription initiation. Curr. Biol. 7, 157-165

Kermicle, J. L. and Alleman, M. (1990). Gametic imprinting in maize in relation to angiosperm life cycle. Dev Suppl. 9-14.

Kiyosue, T. et al. (1999) Control of fertilization-independent endosperm development by the MEDEA polycomb gene in *Arabidopsis*. Proc. Natl. Acad. Sci. USA 96: 4186-4191

Koltunow, A M., Bicknell, R A., and Chaudhury, A M (1995). Apomixis:molecular strategies for the generation of genetically identical seeds without fertilisation. Plant Physiol. 108, 1345-1352.

Krannitz, P G., Aarssen, L W., and Dow, J M. (1991). The effect of genetically based differences in seed size on seedling survival in *Arabidopsis thaliana* (*Brassicaceae*). Am. J. Bot. 78, 446-450.

Laherty, C. D.; Yang, W.-M.; Sun, J. M.; Davie, J. R.; Seto, E. and Eisenman, R. N. (1997) Histone Deacetylases Associated with the mSin3 Corepressor Mediate Mad Transcriptional Repression. Cell 89, 349-356

Li, E., Beard, C., and Jaenisch, R. (1993). Role for DNA methylation in genomic imprinting. Nature 366, 362-365.

Lund, G., Messing J, and Viotti, A. (1995). Endosperm-specific demethylation and activation of specific alleles of aipha-tubulin genes in *Zea mays* L. Mol. Gen. Genet. 246, 716-722.

Luo, M. et al. (1999) Genes controlling fertilization-independent seed development in *Arabidopsis thaliana*. Proc. Natl. Acad. Sci. USA 96: 296-301

Manga and Yadav. (1995). Effect of seed size on developmental traits and ability to tolerate drought in pearl-millet. J. Arid Environments 29, 169-172.

Marshall, D L. (1986). Effect of seed size on seedling success in three species of *Sesbania* (*Fabaceae*). American Journal of Botany 73, 457-464.

Martienssen, R. A. and Richards, E. J. (1995) DNA methylation in eukaryotes. Curr. Opin. Genet. Dev. 5, 234-242

Matzke, M. A. and Matzke, A. J. M. (1995) How and why do plants inactivate homologous (trans)genes? Plant Physiol. 107, 679-685

Nan, X.; Ng, H.-H.; Johnson, C. A.; Laherty, C. D.; Turner, B. M.; Eisenman, R. N. and Bird, A. (1998) Transcriptional repression by the methyl CpG-binding protein MeCP2 involves a histone deacetylase complex. Nature 393, 386-389

Napoli, C., Lemieux, C. and Jorgensen, R. (1990) Introduction of a chimeric chalcone synthase gene into Petunia results in reversible co-suppression of homologous genes in trans, Plant Cell 2, 279-289

Ohad, N. et al. (1996) A mutation that allows endosperm development without fertilization. Proc. Natl. Acad. Sci. USA 93: 5319-5324

Ohad, N. et al. (1999) Mutations in FIE, a WD polycomb group gene, allow endosperm development without fertilization. Plant Cell 11: 407-415

Pazin, M. J. and Kadonaga, J. T. (1997) What's up and down with histone deacetylation and transcription? Cell 89, 325-328

Razin, A. (1998) CpG methylation, chromatin structure and gene silencing—a tree-way connection. EMBO-J 17, 4905-4908

Reiser, L. et al (1995). The BELL gene encodes a homeodomain protein involved in pattern-formation in the *Arabidopsis* ovule primordium. Cell 83, 735-742.

Roberts, M. R., Foster, G. D., Draper, J. and Scott, R. J. (1993). Gametophytic and sporophytic expression of an anther-specific *Arabidopsis thaliana* gene. Plant J. 3, 111-120.

Roekel, P., Oancia, T., and Drevet, J R. (1998). Phenotypic alterations and component analaysis of seed yield in transgenic *Brasicca napus* plants expressing the tzs gene. Physiologica Plantarum, 102, 243-249.

Ronemus, M J., Galbiati, M., Ticknor, C., Chen, J C., and Dellaporta, S L. (1996). Demethylation-induced developmental pleiotropy in *Arabidopsis*. Science 273, 654-657.

Schaal, B A. (1980). Reproductive capacity and seed size in *Lupinus texensis*. American Journal of Botany 67, 703-709.

Scott R J, Spielman M, Bailey J and Dickinson H G. (1998) Parent-of-origin effects on seed development in *Arabidopsis thaliana*. Development 125, 3329-3341.

Sessions, A., Yanofsky, M F. and Weigel, D. (1998). Patterning the floral meristem. Cell and Devel. Biol. 9, 221-226.

Solter, D. (1998). Differential imprinting and expression of maternal and paternal genomes. Ann. Rev. Genet. 22 127-146.

Stoskopf, N C., Tomes, D T., and Christie, B R. (1993). Plant Breeding. Theory and Practice. Westview Press, Boulder USA. Chapter 17.

Vongs, A., Kakutani, T., Martienssen, R. A. and Richards, E. J. (1993). *Arabidopsis thaliana* DNA methylation mutants. Science 260, 1926-1928.

Winn, A A. (1985). Effects of seed size and microsite on seedling emergence of *Prunella vulgaris* in four habitats. Journal of Ecology 73, 831-840.

Wulff, R D. (1986). Seed size variation in *Desmondium paniculatumII*. Effects on seedling growth and physiological performance. Journal of Ecology 74, 99-114.

The invention claimed is:

1. A method for the production of modified endosperm, which comprises the step of introducing a nucleic acid molecule into a plant, the nucleic acid molecule comprising a promoter that targets expression to female germ line cells and a sequence whose transcription product comprises a partial or full-length *Arabidopsis* DNA methyltransferase 1 (Met1) sequence, wherein the introduced nucleic acid is effective for down-regulating one or more DNA methylating enzymes present in the plant, whereby the degree of DNA methylation of nucleic acid in the plant is reduced as compared to a control plant.

2. The method as claimed in claim 1 wherein the transcription product comprises an antisense nucleic acid.

3. A method for the production of modified endosperm, which comprises the step of introducing a nucleic acid molecule into a plant, the nucleic acid molecule comprising a promoter that targets expression to female germ line cells and a sequence whose transcription product comprises a partial or full-length *Z. mays* DNA sequence orthologous to the *Arabidopsis* DNA methyltransferase 1 (Met1) sequence, wherein the introduced nucleic acid is effective for down-regulating one or more DNA methylating enzymes present in the plant, whereby the degree of DNA methylation of nucleic acid in the plant is reduced as compared to a control plant.

4. The method as claimed in claim 3, wherein the transcription product comprises an antisense nucleic acid.

5. The method as claimed in claim 1, wherein the plant is a dicotyledonous plant.

6. The method as claimed in claim 1, wherein the transcription product down-regulates one DNA methylating enzyme.

7. The method as claimed in claim 1, wherein the transcription product comprises a full or partial sense copy of the *Arabidopsis* DNA methyltransferase 1 (Met1) sequence.

8. The method as claimed in claim 7, wherein the sense copy is a partial sense copy.

9. A method as claimed in claim 3, wherein the transcription product comprises a full or partial sense copy of the *Z. mays* sequence.

10. A method as claimed in claim 7, wherein the plant is a dicotyledonous plant.

11. The method as claimed in claim 3, wherein the plant is a dicotyledonous plant.

12. The method as claimed in claim 1, wherein the promoter targets expression in female gametic cells.

13. The method as claimed in claim 12, wherein the transcription product comprises an antisense nucleic acid.

14. The method as claimed in claim 12, wherein the transcription product comprises a partial sense copy of the *Arabidopsis* DNA methyltransferase 1 (Met1) sequence.

15. The method as claimed in claim 12, wherein the plant is a dicotyledonous plant.

16. The method as claimed in claim 12, wherein the plant is a monocotyledonous plant.

17. The method as claimed in claim 15, wherein the plant is a *Brassica* plant.

18. The method as claimed in claim 15, wherein the plant is a *B. napus* plant.

19. The method as claimed in claim 16, wherein the plant is a *Zea mays* plant.

20. The method as claimed in claim 3, wherein the promoter targets expression to female gametic cells.

21. The method as claimed in claim 20, wherein the transcription product comprises an antisense nucleic acid.

22. The method as claimed in claim 20, wherein the transcription product comprises a partial sense copy of the *Z. mays* sequence orthologous to *Arabidopsis* DNA methyltransferase 1 (Met1) sequence.

23. The method as claimed in claim 20, wherein the plant is a dicotyledonous plant.

24. The method as claimed in claim 20, wherein the plant is a monocotyledonous plant.

25. The method as claimed in claim 23, wherein the plant is a *Brassica* plant.

26. The method as claimed in claim 23, wherein the plant is a *B. napus* plant.

27. A method as claimed in claim 24, wherein the plant is a *Zea mays* plant.

* * * * *

```
                        SEQUENCE LISTING

<160> NUMBER OF SEQ ID NOS: 6

<210> SEQ ID NO 1
<211> LENGTH: 34
<212> TYPE: DNA
<213> ORGANISM: Artificial Sequence
<220> FEATURE:
<223> OTHER INFORMATION: Description of Artificial Sequence: Primer

<400> SEQUENCE: 1
ccgaattctt caagcaaaag aatctttgtg ggag                              34

<210> SEQ ID NO 2
<211> LENGTH: 34
<212> TYPE: DNA
<213> ORGANISM: Artificial Sequence
<220> FEATURE:
<223> OTHER INFORMATION: Description of Artificial Sequence: Primer

<400> SEQUENCE: 2
cggtacctat aagccctagc tgaagtataa acac                              34

<210> SEQ ID NO 3
<211> LENGTH: 37
<212> TYPE: DNA
<213> ORGANISM: Artificial Sequence
<220> FEATURE:
<223> OTHER INFORMATION: Description of Artificial Sequence: Primer

<400> SEQUENCE: 3
ccgaattcaa gcttcttaag aattatagta gcacttg                           37

<210> SEQ ID NO 4
<211> LENGTH: 39
<212> TYPE: DNA
<213> ORGANISM: Artificial Sequence
<220> FEATURE:
<223> OTHER INFORMATION: Description of Artificial Sequence: Primer

<400> SEQUENCE: 4
gggtaccttc tctctttgtt taatctttt gttgaagag                          39
```

```
<210> SEQ ID NO 5
<211> LENGTH: 33
<212> TYPE: DNA
<213> ORGANISM: Artificial Sequence
<220> FEATURE:
<223> OTHER INFORMATION: Description of Artificial Sequence: Primer

<400> SEQUENCE: 5
actcgagatt ttgaaaatgg tggaaaatgg ggc                             33

<210> SEQ ID NO 6
<211> LENGTH: 34
<212> TYPE: DNA
<213> ORGANISM: Artificial Sequence
<220> FEATURE:
<223> OTHER INFORMATION: Description of Artificial Sequence: Primer

<400> SEQUENCE: 6
acccgggtgg ttatctaggg ttggtgttga ggag                            34
```